(12) United States Patent
Say et al.

(10) Patent No.: US 8,168,051 B2
(45) Date of Patent: May 1, 2012

(54) SENSOR FOR DETERMINATION OF GLUCOSE

(75) Inventors: James Say, Alameda, CA (US); Michael F. Tomasco, Cupertino, CA (US); Adam Heller, Austin, TX (US); Yoram Gal, Kibbutz Yagur (IL); Behrad Aria, Alameda, CA (US); Ephraim Heller, Oakland, CA (US); Phillip John Plante, Sunnyvale, CA (US); Mark S. Vreeke, Alameda, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 412 days.

(21) Appl. No.: 11/929,925

(22) Filed: Oct. 30, 2007

(65) Prior Publication Data

US 2008/0281175 A1 Nov. 13, 2008

Related U.S. Application Data

(63) Continuation of application No. 11/204,551, filed on Aug. 16, 2005, now Pat. No. 7,721,412, which is a continuation of application No. 10/405,765, filed on Mar. 31, 2003, now Pat. No. 6,973,706, which is a continuation of application No. 09/598,776, filed on Jun. 16, 2000, now abandoned, which is a continuation of application No. 09/034,422, filed on Mar. 4, 1998, now Pat. No. 6,103,033.

(51) Int. Cl.
*G01N 27/327* (2006.01)
(52) U.S. Cl. ............... 204/403.13; 204/403.01; 600/345
(58) Field of Classification Search ............. 204/403.01, 204/403.11, 403.13; 600/345, 347
See application file for complete search history.

(56) References Cited

U.S. PATENT DOCUMENTS

| | | | |
|---|---|---|---|
| 3,260,656 A | 7/1966 | Ross, Jr. |
| 3,653,841 A | 4/1972 | Klein |
| 3,719,564 A | 3/1973 | Lilly, Jr. et al. |
| 3,776,832 A | 12/1973 | Oswin et al. |
| 3,837,339 A | 9/1974 | Aisenberg et al. |
| 3,911,901 A | 10/1975 | Niedrach et al. |
| 3,926,760 A | 12/1975 | Allen et al. |
| 3,972,320 A | 8/1976 | Kalman |
| 3,979,274 A | 9/1976 | Newman |
| 4,008,717 A | 2/1977 | Kowarski |

(Continued)

FOREIGN PATENT DOCUMENTS

DE 2903216 8/1979

(Continued)

OTHER PUBLICATIONS

Needle gauge comparison chart from Wikipedia.org, date unknown.*

(Continued)

*Primary Examiner* — Kaj K Olsen
(74) *Attorney, Agent, or Firm* — Jackson & Co., LLP

(57) ABSTRACT

A process for the manufacture of small sensors with reproducible surfaces, including electrochemical sensors. One process includes forming channels in the surface of a substrate and disposing a conductive material in the channels to form an electrode. The conductive material can also be formed on the substrate by other impact and non-impact methods. In a preferred embodiment, the method includes cutting the substrate to form a sensor having a connector portion and a transcutaneous portion, the two portions having edges that define one continuous straight line.

15 Claims, 12 Drawing Sheets

U.S. PATENT DOCUMENTS

| | | |
|---|---|---|
| 4,016,866 A | 4/1977 | Lawton |
| 4,055,175 A | 10/1977 | Clemens et al. |
| 4,059,406 A | 11/1977 | Fleet |
| 4,076,596 A | 2/1978 | Connery et al. |
| 4,098,574 A | 7/1978 | Dappen |
| 4,100,048 A | 7/1978 | Pompei et al. |
| 4,151,845 A | 5/1979 | Clemens |
| 4,168,205 A | 9/1979 | Danninger et al. |
| 4,172,770 A | 10/1979 | Semersky et al. |
| 4,178,916 A | 12/1979 | McNamara |
| 4,184,429 A | 1/1980 | Widmer |
| 4,206,755 A | 6/1980 | Klein |
| 4,210,156 A | 7/1980 | Bennett |
| 4,224,125 A | 9/1980 | Nakamura et al. |
| 4,240,438 A | 12/1980 | Updike et al. |
| 4,247,297 A | 1/1981 | Berti et al. |
| 4,340,458 A | 7/1982 | Lerner et al. |
| 4,352,960 A | 10/1982 | Dormer et al. |
| 4,356,074 A | 10/1982 | Johnson |
| 4,360,016 A | 11/1982 | Sarrine |
| 4,365,637 A | 12/1982 | Johnson |
| 4,366,033 A | 12/1982 | Richter et al. |
| 4,375,399 A | 3/1983 | Havas et al. |
| 4,384,586 A | 5/1983 | Christiansen |
| 4,390,621 A | 6/1983 | Bauer |
| 4,401,122 A | 8/1983 | Clark, Jr. |
| 4,404,066 A | 9/1983 | Johnson |
| 4,418,148 A | 11/1983 | Oberhardt |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,450,842 A | 5/1984 | Zick et al. |
| 4,458,686 A | 7/1984 | Clark, Jr. |
| 4,461,691 A | 7/1984 | Frank |
| 4,469,110 A | 9/1984 | Slama |
| 4,477,314 A | 10/1984 | Richter et al. |
| 4,484,987 A | 11/1984 | Gough |
| 4,522,690 A | 6/1985 | Venkatasetty |
| 4,524,114 A | 6/1985 | Samuels et al. |
| 4,526,661 A | 7/1985 | Steckhan et al. |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,560,534 A | 12/1985 | Kung et al. |
| 4,571,292 A | 2/1986 | Liu et al. |
| 4,573,994 A | 3/1986 | Fischell et al. |
| 4,581,336 A | 4/1986 | Malloy et al. |
| 4,592,893 A | 6/1986 | Poppe et al. |
| 4,595,011 A | 6/1986 | Phillips |
| 4,610,741 A | 9/1986 | Mase et al. |
| 4,619,754 A | 10/1986 | Niki et al. |
| 4,627,445 A | 12/1986 | Garcia et al. |
| 4,627,908 A | 12/1986 | Miller |
| 4,633,878 A | 1/1987 | Bombardieri |
| 4,637,403 A | 1/1987 | Garcia et al. |
| 4,650,547 A | 3/1987 | Gough |
| 4,653,513 A | 3/1987 | Dombrowski |
| 4,654,197 A | 3/1987 | Lilja et al. |
| 4,655,880 A | 4/1987 | Liu |
| 4,655,885 A | 4/1987 | Hill et al. |
| 4,671,288 A | 6/1987 | Gough |
| 4,679,562 A | 7/1987 | Luksha |
| 4,680,268 A | 7/1987 | Clark, Jr. |
| 4,682,602 A | 7/1987 | Prohaska |
| 4,684,537 A | 8/1987 | Graetzel et al. |
| 4,685,463 A | 8/1987 | Williams |
| 4,703,756 A | 11/1987 | Gough et al. |
| 4,711,245 A | 12/1987 | Higgins et al. |
| 4,714,874 A * | 12/1987 | Morris et al. ............ 324/601 |
| 4,717,673 A | 1/1988 | Wrighton et al. |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,757,022 A | 7/1988 | Shults et al. |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |
| 4,781,798 A | 11/1988 | Gough |
| 4,784,736 A | 11/1988 | Lonsdale et al. |
| 4,787,398 A | 11/1988 | Garcia et al. |
| 4,787,837 A | 11/1988 | Bell |
| 4,795,542 A | 1/1989 | Ross et al. |
| 4,795,707 A | 1/1989 | Niiyama et al. |
| 4,796,634 A | 1/1989 | Huntsman et al. |
| 4,805,624 A | 2/1989 | Yao et al. |
| 4,813,424 A | 3/1989 | Wilkins |
| 4,815,469 A | 3/1989 | Cohen et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| RE32,947 E | 6/1989 | Dormer et al. |
| 4,840,893 A | 6/1989 | Hill et al. |
| 4,848,351 A | 7/1989 | Finch |
| 4,871,351 A | 10/1989 | Feingold |
| 4,871,440 A | 10/1989 | Nagata et al. |
| 4,874,500 A | 10/1989 | Madou et al. |
| 4,890,620 A | 1/1990 | Gough |
| 4,894,137 A | 1/1990 | Takizawa et al. |
| 4,895,147 A | 1/1990 | Bodicky et al. |
| 4,897,162 A | 1/1990 | Lewandowski et al. |
| 4,897,173 A | 1/1990 | Nankai et al. |
| 4,909,908 A | 3/1990 | Ross et al. |
| 4,911,794 A | 3/1990 | Parce et al. |
| 4,917,274 A | 4/1990 | Asa et al. |
| 4,917,800 A | 4/1990 | Lonsdale et al. |
| 4,919,141 A | 4/1990 | Zier et al. |
| 4,919,767 A | 4/1990 | Vadgama et al. |
| 4,923,442 A | 5/1990 | Segall et al. |
| 4,923,586 A | 5/1990 | Katayama et al. |
| 4,927,516 A | 5/1990 | Yamaguchi et al. |
| 4,934,369 A | 6/1990 | Maxwell |
| 4,935,105 A | 6/1990 | Churchouse |
| 4,935,345 A | 6/1990 | Guilbeau et al. |
| 4,938,860 A | 7/1990 | Wogoman |
| 4,944,299 A | 7/1990 | Silvian |
| 4,950,378 A | 8/1990 | Nagata |
| 4,953,552 A | 9/1990 | DeMarzo |
| 4,954,129 A | 9/1990 | Giuliani et al. |
| 4,955,380 A | 9/1990 | Edell |
| 4,969,468 A | 11/1990 | Byers et al. |
| 4,970,145 A | 11/1990 | Bennetto et al. |
| 4,974,929 A | 12/1990 | Curry |
| 4,986,271 A | 1/1991 | Wilkins |
| 4,994,167 A | 2/1991 | Shults et al. |
| 5,001,054 A | 3/1991 | Wagner |
| 5,025,798 A | 6/1991 | Schindele |
| 5,058,592 A | 10/1991 | Whisler |
| 5,063,081 A | 11/1991 | Cozzette et al. |
| 5,070,535 A | 12/1991 | Hochmair et al. |
| 5,082,550 A | 1/1992 | Rishpon et al. |
| 5,082,786 A | 1/1992 | Nakamoto |
| 5,089,112 A | 2/1992 | Skotheim et al. |
| 5,089,320 A | 2/1992 | Straus et al. |
| 5,095,904 A | 3/1992 | Seligman et al. |
| 5,101,814 A | 4/1992 | Palti |
| 5,108,564 A | 4/1992 | Szuminsky et al. |
| 5,108,889 A | 4/1992 | Smith et al. |
| 5,109,850 A | 5/1992 | Blanco et al. |
| 5,120,420 A | 6/1992 | Nankai et al. |
| 5,126,034 A | 6/1992 | Carter et al. |
| 5,128,015 A | 7/1992 | Szuminsky et al. |
| 5,133,856 A | 7/1992 | Yamaguchi et al. |
| 5,135,003 A | 8/1992 | Souma |
| 5,141,868 A | 8/1992 | Shanks et al. |
| 5,161,532 A | 11/1992 | Joseph |
| 5,165,407 A | 11/1992 | Wilson et al. |
| 5,174,291 A | 12/1992 | Schoonen et al. |
| 5,190,041 A | 3/1993 | Palti |
| 5,192,416 A | 3/1993 | Wang et al. |
| 5,198,367 A | 3/1993 | Aizawa et al. |

| Patent No. | Date | Inventor |
|---|---|---|
| 5,201,324 A | 4/1993 | Swierczek |
| 5,202,261 A | 4/1993 | Musho et al. |
| 5,205,920 A | 4/1993 | Oyama et al. |
| 5,208,154 A | 5/1993 | Weaver et al. |
| 5,209,229 A | 5/1993 | Gilli |
| 5,217,480 A | 6/1993 | Haber et al. |
| 5,217,595 A | 6/1993 | Smith et al. |
| 5,229,282 A | 7/1993 | Yoshioka et al. |
| 5,250,439 A | 10/1993 | Musho et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,106 A | 11/1993 | McAleer et al. |
| 5,269,891 A | 12/1993 | Colin |
| 5,271,815 A | 12/1993 | Wong |
| 5,279,294 A | 1/1994 | Anderson et al. |
| 5,284,567 A | 2/1994 | Matson |
| 5,286,362 A | 2/1994 | Hoenes et al. |
| 5,286,364 A | 2/1994 | Yacynych et al. |
| 5,288,636 A | 2/1994 | Pollmann et al. |
| 5,293,546 A | 3/1994 | Tadros et al. |
| 5,318,584 A | 6/1994 | Lange et al. |
| 5,320,098 A | 6/1994 | Davidson |
| 5,320,725 A | 6/1994 | Gregg et al. |
| 5,322,063 A | 6/1994 | Allen et al. |
| 5,337,747 A | 8/1994 | Neftel |
| 5,352,348 A | 10/1994 | Young et al. |
| 5,352,351 A | 10/1994 | White et al. |
| 5,354,447 A | 10/1994 | Uenoyama et al. |
| 5,356,786 A | 10/1994 | Heller et al. |
| 5,366,609 A | 11/1994 | White et al. |
| 5,368,028 A | 11/1994 | Palti |
| 5,372,133 A | 12/1994 | Hogen Esch |
| 5,376,251 A | 12/1994 | Kaneko et al. |
| 5,378,628 A | 1/1995 | Gratzel et al. |
| 5,384,028 A * | 1/1995 | Ito ............................ 257/253 |
| 5,387,327 A | 2/1995 | Khan |
| 5,390,671 A | 2/1995 | Lord et al. |
| 5,391,250 A | 2/1995 | Cheney et al. |
| 5,395,504 A | 3/1995 | Saurer et al. |
| 5,411,647 A | 5/1995 | Johnson et al. |
| 5,424,035 A | 6/1995 | Hones et al. |
| 5,429,735 A | 7/1995 | Johnson et al. |
| 5,431,806 A | 7/1995 | Suzuki et al. |
| 5,437,999 A | 8/1995 | Diebold et al. |
| 5,438,271 A | 8/1995 | White et al. |
| 5,469,846 A | 11/1995 | Khan |
| 5,494,562 A | 2/1996 | Maley et al. |
| 5,496,453 A | 3/1996 | Uenoyama et al. |
| 5,497,772 A | 3/1996 | Schulman et al. |
| 5,508,171 A | 4/1996 | Walling et al. |
| 5,509,410 A | 4/1996 | Hill et al. |
| 5,510,266 A | 4/1996 | Bonner et al. |
| 5,512,159 A | 4/1996 | Yoshioka et al. |
| 5,513,636 A * | 5/1996 | Palti ............................ 600/352 |
| 5,518,006 A | 5/1996 | Mawhirt et al. |
| 5,520,731 A | 5/1996 | Esser et al. |
| 5,531,878 A | 7/1996 | Vadgama et al. |
| 5,545,191 A | 8/1996 | Mann et al. |
| 5,547,555 A | 8/1996 | Schwartz et al. |
| 5,560,357 A | 10/1996 | Faupel et al. |
| 5,565,085 A | 10/1996 | Ikeda et al. |
| 5,567,302 A | 10/1996 | Song et al. |
| 5,568,806 A | 10/1996 | Cheney, II et al. |
| 5,569,186 A | 10/1996 | Lord et al. |
| 5,572,140 A | 11/1996 | Lim et al. |
| 5,575,403 A | 11/1996 | Charlton et al. |
| 5,575,895 A | 11/1996 | Ikeda et al. |
| 5,582,184 A | 12/1996 | Erickson et al. |
| 5,582,697 A | 12/1996 | Ikeda et al. |
| 5,582,698 A | 12/1996 | Flaherty et al. |
| 5,586,553 A | 12/1996 | Halili et al. |
| 5,589,326 A | 12/1996 | Deng et al. |
| 5,593,852 A | 1/1997 | Heller et al. |
| 5,596,150 A | 1/1997 | Arndt et al. |
| 5,617,851 A | 4/1997 | Lipkovker |
| 5,628,890 A | 5/1997 | Carter et al. |
| 5,630,986 A | 5/1997 | Charlton et al. |
| 5,632,410 A | 5/1997 | Moulton et al. |
| 5,651,869 A | 7/1997 | Yoshioka et al. |
| 5,653,864 A | 8/1997 | Gotoh et al. |
| 5,658,443 A | 8/1997 | Yamamoto et al. |
| 5,660,163 A | 8/1997 | Schulman et al. |
| 5,666,966 A | 9/1997 | Horie et al. |
| 5,670,031 A | 9/1997 | Hintsche et al. |
| 5,680,858 A | 10/1997 | Hansen et al. |
| 5,681,632 A | 10/1997 | Kitaura et al. |
| 5,682,233 A | 10/1997 | Brinda |
| 5,683,562 A | 11/1997 | Schaffar et al. |
| 5,695,623 A | 12/1997 | Michel et al. |
| 5,708,247 A | 1/1998 | McAleer et al. |
| 5,711,861 A | 1/1998 | Ward et al. |
| 5,711,862 A | 1/1998 | Sakoda et al. |
| 5,741,211 A | 4/1998 | Renirie et al. |
| 5,743,861 A | 4/1998 | Columbus et al. |
| 5,759,364 A | 6/1998 | Charlton et al. |
| 5,777,060 A | 7/1998 | Van Antwerp |
| 5,786,584 A | 7/1998 | Button et al. |
| 5,791,344 A * | 8/1998 | Schulman et al. ............ 600/347 |
| 5,800,420 A | 9/1998 | Gross et al. |
| 5,807,375 A | 9/1998 | Gross et al. |
| 5,820,551 A | 10/1998 | Hill et al. |
| 5,822,715 A | 10/1998 | Worthington et al. |
| 5,830,341 A | 11/1998 | Gilmartin |
| 5,840,020 A | 11/1998 | Heinonen et al. |
| 5,873,990 A | 2/1999 | Wojciechowski et al. |
| 5,885,429 A | 3/1999 | Friese et al. |
| 5,906,921 A | 5/1999 | Ikeda et al. |
| 5,951,492 A | 9/1999 | Douglas et al. |
| 5,951,836 A | 9/1999 | McAleer et al. |
| 5,954,643 A | 9/1999 | Van Antwerp et al. |
| 5,964,993 A | 10/1999 | Blubaugh, Jr. et al. |
| 5,971,941 A | 10/1999 | Simons et al. |
| 5,972,199 A | 10/1999 | Heller et al. |
| 5,989,409 A | 11/1999 | Kurnik et al. |
| 5,997,817 A | 12/1999 | Crismore et al. |
| 6,004,441 A | 12/1999 | Fujiwara et al. |
| 6,020,110 A | 2/2000 | Williams et al. |
| 6,021,339 A | 2/2000 | Saito et al. |
| 6,022,366 A | 2/2000 | Scraga |
| 6,027,459 A | 2/2000 | Shain et al. |
| 6,036,924 A | 3/2000 | Simons et al. |
| 6,046,056 A | 4/2000 | Parce et al. |
| 6,063,039 A | 5/2000 | Cunningham et al. |
| 6,071,249 A | 6/2000 | Cunningham et al. |
| 6,071,251 A | 6/2000 | Cunningham et al. |
| 6,074,725 A | 6/2000 | Kennedy |
| 6,093,156 A | 7/2000 | Cunningham et al. |
| 6,099,484 A | 8/2000 | Douglas et al. |
| 6,103,033 A | 8/2000 | Say et al. |
| 6,120,676 A | 9/2000 | Heller et al. |
| 6,143,164 A | 11/2000 | Heller et al. |
| 6,156,051 A | 12/2000 | Schraga |
| 6,190,398 B1 | 2/2001 | Schraga |
| 6,192,891 B1 | 2/2001 | Gravel et al. |
| 6,206,841 B1 | 3/2001 | Cunningham et al. |
| 6,210,420 B1 | 4/2001 | Mauze et al. |
| 6,283,926 B1 | 9/2001 | Cunningham et al. |
| 6,283,982 B1 | 9/2001 | Levaughn et al. |
| 6,299,757 B1 | 10/2001 | Feldman et al. |
| 6,306,104 B1 | 10/2001 | Cunningham et al. |
| 6,306,152 B1 | 10/2001 | Verdonk et al. |
| 6,346,114 B1 | 2/2002 | Schraga |
| 6,352,514 B1 | 3/2002 | Douglas et al. |
| 6,368,141 B1 | 4/2002 | VanAntwerp et al. |
| 6,409,740 B1 | 6/2002 | Kuhr et al. |
| 6,436,255 B2 | 8/2002 | Yamamoto et al. |
| 6,506,168 B1 | 1/2003 | Fathallah et al. |
| 6,540,891 B1 | 4/2003 | Stewart et al. |
| 6,579,690 B1 | 6/2003 | Bonnecaze et al. |
| 6,599,407 B2 | 7/2003 | Taniike et al. |
| 6,607,658 B1 | 8/2003 | Heller et al. |
| 6,616,819 B1 | 9/2003 | Liamos et al. |
| 6,638,772 B1 | 10/2003 | Douglas et al. |
| 6,740,215 B1 | 5/2004 | Nakaminami et al. |
| 6,885,196 B2 | 4/2005 | Taniike et al. |
| 6,973,706 B2 | 12/2005 | Say et al. |

| | | | |
|---|---|---|---|
| 7,335,294 B2 | 2/2008 | Heller et al. | |
| 7,721,412 B2 | 5/2010 | Say et al. | |
| 2003/0143113 A2 | 7/2003 | Yuzhakov et al. | |
| 2003/0188427 A1 | 10/2003 | Say et al. | |
| 2004/0002682 A1 | 1/2004 | Kovelman et al. | |
| 2006/0042080 A1 | 3/2006 | Say et al. | |
| 2008/0047129 A1 | 2/2008 | Say et al. | |
| 2008/0272007 A1 | 11/2008 | Say et al. | |
| 2008/0275323 A1 | 11/2008 | Say et al. | |
| 2008/0275423 A1 | 11/2008 | Say et al. | |
| 2008/0276455 A1 | 11/2008 | Say et al. | |
| 2008/0281175 A1 | 11/2008 | Say et al. | |
| 2008/0281176 A1 | 11/2008 | Say et al. | |
| 2008/0281177 A1 | 11/2008 | Say et al. | |
| 2008/0287759 A1 | 11/2008 | Say et al. | |
| 2008/0287760 A1 | 11/2008 | Say et al. | |
| 2008/0295324 A1 | 12/2008 | Say et al. | |

FOREIGN PATENT DOCUMENTS

| | | |
|---|---|---|
| DE | 227029 | 9/1985 |
| DE | 3740149 | 6/1989 |
| DE | 3934299 | 10/1990 |
| EP | 0010375 | 4/1980 |
| EP | 0026995 | 4/1981 |
| EP | 0048090 | 3/1982 |
| EP | 0078636 | 5/1983 |
| EP | 0080304 | 6/1983 |
| EP | 0096288 | 12/1983 |
| EP | 0125139 | 11/1984 |
| EP | 0127958 | 12/1984 |
| EP | 0136362 | 4/1985 |
| EP | 0170375 | 2/1986 |
| EP | 0177743 | 4/1986 |
| EP | 0184909 | 6/1986 |
| EP | 0193676 | 9/1986 |
| EP | 0206218 | 12/1986 |
| EP | 0230472 | 8/1987 |
| EP | 0241309 | 10/1987 |
| EP | 0245073 | 11/1987 |
| EP | 0255291 | 2/1988 |
| EP | 0278647 | 8/1988 |
| EP | 0359831 | 3/1990 |
| EP | 0368209 | 5/1990 |
| EP | 0390390 | 10/1990 |
| EP | 0396788 | 11/1990 |
| EP | 0400918 | 12/1990 |
| EP | 0453283 | 10/1991 |
| EP | 0470290 | 2/1992 |
| EP | 0563795 | 3/1993 |
| EP | 1060707 | 12/2000 |
| GB | 1394171 | 5/1975 |
| GB | 1599241 | 9/1981 |
| GB | 2073891 | 10/1981 |
| GB | 2154003 | 8/1985 |
| GB | 2204408 | 11/1988 |
| GB | 2254436 | 10/1992 |
| GB | 2287472 | 9/1995 |
| JP | 54-041191 | 4/1979 |
| JP | 55-010581 | 1/1980 |
| JP | 55-010583 | 1/1980 |
| JP | 55-010584 | 1/1980 |
| JP | 55-012406 | 1/1980 |
| JP | 56-163447 | 12/1981 |
| JP | 57-070448 | 4/1982 |
| JP | 59-147249 | 8/1984 |
| JP | 60-173457 | 9/1985 |
| JP | 60-173458 | 9/1985 |
| JP | 60-173459 | 9/1985 |
| JP | 61-090050 | 5/1986 |
| JP | 62-085855 | 4/1987 |
| JP | 62-114747 | 5/1987 |
| JP | 63-058149 | 3/1988 |
| JP | 63-128252 | 5/1988 |
| JP | 63-139246 | 6/1988 |
| JP | 63-294799 | 12/1988 |
| JP | 63-317757 | 12/1988 |
| JP | 63-317758 | 12/1988 |
| JP | 1-114746 | 5/1989 |
| JP | 1-114747 | 5/1989 |
| JP | 1-124060 | 5/1989 |
| JP | 1-134244 | 5/1989 |
| JP | 1-156658 | 6/1989 |
| JP | 2-019758 | 1/1990 |
| JP | 2-062958 | 3/1990 |
| JP | 2-120655 | 5/1990 |
| JP | 2-287145 | 11/1990 |
| JP | 2-310457 | 12/1990 |
| JP | 3-026956 | 2/1991 |
| JP | 3-028752 | 2/1991 |
| JP | 3-202764 | 9/1991 |
| JP | 3-293556 | 12/1991 |
| JP | 4-194660 | 7/1992 |
| JP | 5-072171 | 3/1993 |
| JP | 5-196595 | 8/1993 |
| JP | 6-190050 | 7/1994 |
| JP | 7-055757 | 3/1995 |
| JP | 7-072585 | 3/1995 |
| JP | 7-286987 | 10/1995 |
| JP | 8-285814 | 11/1996 |
| JP | 8-285815 | 11/1996 |
| JP | 9-021778 | 1/1997 |
| JP | 9-101280 | 4/1997 |
| JP | 9-285459 | 11/1997 |
| JP | 10-170471 | 6/1998 |
| SU | 1281988 | 1/1987 |
| WO | WO-85/05119 | 11/1985 |
| WO | WO-86/00513 | 1/1986 |
| WO | WO-89/08713 | 9/1989 |
| WO | WO-90/05300 | 5/1990 |
| WO | WO-90/05910 | 5/1990 |
| WO | WO-91/01680 | 2/1991 |
| WO | WO-91/04704 | 4/1991 |
| WO | WO-91/15993 | 10/1991 |
| WO | WO-92/13271 | 8/1992 |
| WO | WO-94/20602 | 9/1994 |
| WO | WO-94/27140 | 11/1994 |
| WO | WO-95/13534 | 5/1995 |
| WO | WO-95/28634 | 10/1995 |
| WO | WO 95/28634 * | 10/1995 |
| WO | WO 96/00614 * | 1/1996 |
| WO | WO 96/00614 A1 * | 1/1996 |
| WO | WO-96/06947 | 3/1996 |
| WO | WO-96/21150 | 7/1996 |
| WO | WO-96/30431 | 10/1996 |
| WO | WO-97/00441 | 1/1997 |
| WO | WO-97/02847 | 1/1997 |
| WO | WO-97/18464 | 5/1997 |
| WO | WO-97/19344 | 5/1997 |
| WO | WO-97/27473 | 7/1997 |
| WO | WO-97/42882 | 11/1997 |
| WO | WO-97/42883 | 11/1997 |
| WO | WO-97/42886 | 11/1997 |
| WO | WO-97/42888 | 11/1997 |
| WO | WO-97/43962 | 11/1997 |
| WO | WO-00/78210 | 12/2000 |
| WO | WO-01/64105 | 9/2001 |
| WO | WO-01/72220 | 10/2001 |
| WO | WO-01/73395 | 10/2001 |

OTHER PUBLICATIONS

U.S. Appl. No. 09/598,776, Say, et al.
U.S. Appl. No. 11/929,906, Say, et al.
U.S. Appl. No. 11/929,945, Say, et al.
U.S. Appl. No. 11/929,952, Say, et al.
U.S. Appl. No. 11/929,959, Say, et al.
U.S. Appl. No. 11/929,964, Say, et al.
U.S. Appl. No. 11/929,967, Say, et al.
U.S. Appl. No. 11/929,986, Say, et al.
U.S. Appl. No. 11/930,004, Say, et al.
U.S. Appl. No. 11/930,011, Say, et al.
Abruna, H. D., et al., "Rectifying Interfaces Using Two-Layer Films of Electrochemically Polymerized Vinylpyridine and Vinylbipyridine Complexes of Ruthenium and Iron on Electrodes", *Journal of the American Chemical Society*, vol. 103, No. 1, 1981, pp. 1-5.

Albery, W. J., et al., "Amperometric Enzyme Electrodes Part II: Conducting Salts as Electrode Materials for the Oxidation of Glucose Oxidase", *Journal of ElectroAnalytical Chemistry*, vol. 194, 1985, pp. 223-235.

Albery, W. J., et al., "Amperometric Enzyme Electrodes", *Philosophical Transactions of the Royal Society of London*, vol. 316, 1987, pp. 107-119.

Alcock, S. J., et al., "Continuous Analyte Monitoring to Aid Clinical Practice", *IEEE Engineering in Medicine and Biology Magazine*, pp. 319-325.

Anderson, L. B., et al., "Thin-Layer Electrochemistry: Steady-State Methods of Studying Rate Processes", *Journal of ElectroAnalytical Chemistry*, vol. 10, 1965, pp. 295-305.

Bartlett, P. N., et al., "Covalent Binding of Electron Relays to Glucose Oxidase", *Journal of the Chemical Society, Chemical Communications*, 1987, pp. 1603-1604.

Bartlett, P. N., et al., "Modification of Glucose Oxidase by Tetrathiafulvalene", *Journal of the Chemical Society, Chemical Communications*, 1990, pp. 1135-1136.

Bartlett, P. N., et al., "Strategies for the Development of Amperometric Enzyme Electrodes", *Biosensors*, vol. 3, 1987/88, pp. 359-379.

Bindra, D. S., et al., "Design and in Vitro Studies of a Needle-Type Glucose Sensor for Subcutaneous Monitoring", *Analytical Chemistry*, vol. 63, No. 17, 1991, pp. 1692-1696.

Bobbioni-Harsch, E., et al., "Lifespan of Subcutaneous Glucose Sensors and Their Performances During Dynamic Glycaemia Changes in Rats", *Journal of Biomedical Engineering*, vol. 15, 1993, pp. 457-463.

Brandt, J., et al., "Covalent Attachment of Proteins to Polysaccharide Carriers by Means of Benzoquinone", *Biochimica et Biophysica Acta*, vol. 386, 1975, pp. 196-202.

Brownlee, M., et al., "A Glucose-Controlled Insulin-Delivery System: Semisynthetic Insulin Bound to Lectin", *Science*, vol. 206, 1979, 1190-1191.

Cass, A. E., et al., "Ferricinum Ion as an Electron Acceptor for Oxido-Reductases", *Journal of ElectroAnalytical Chemistry*, vol. 190, 1985, pp. 117-127.

Cass, A. E., et al., "Ferrocene-Medicated Enzyme Electrode for Amperometric Determination of Glucose", *Analytical Chemistry*, vol. 56, No. 4, 1984, 667-671.

Castner, J. F., et al., "Mass Transport and Reaction Kinetic Parameters Determined Electrochemically for Immobilized Glucose Oxidase", *Biochemistry*, vol. 23 No. 10, 1984, 2203-2210.

Claremont, D. J., et al., "Biosensors for Continuous in Vivo Glucose Monitoring", *Proceedings of the Annual International Conference of the IEEE Engineering in Medicine and Biology Society*, vol. 10, 1988.

Clark Jr., L. C., et al., "Differential Anodic Enzyme Polarography for the Measurement of Glucose", *Oxygen Transport to Tissue: Instrumentation, Methods, and Physiology*, 1973, pp. 127-133.

Clark Jr., L. C., et al., "Electrode Systems for Continuous Monitoring in Cardiovascular Surgery", *Annals New York Academy of Sciences*, 1962, pp. 29-45.

Clark Jr., L. C., et al., "Long-term Stability of Electroenzymatic Glucose Sensors Implanted in Mice", *American Society of Artificial Internal Organs Transactions*, vol. XXXIV, 1988, pp. 259-265.

Clarke, W. L., et al., "Evaluating Clinical Accuracy of Systems for Self-Monitoring of Blood Glucose", *Diabetes Care*, vol. 10, No. 5, 1987, pp. 622-628.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

Csoregi, E., et al., "Design, Characterization, and One-Point in Vivo Calibration of a Subcutaneously Implanted Glucose Electrode", *Analytical Chemistry*, vol. 66 No. 19, 1994, pp. 3131-3138.

Csoregi, E., et al., "On-Line Glucose Monitoring by Using Microdialysis Sampling and Amperometric Detection Based on 'Wired' Glucose Oxidase in Carbon Paste", *Mikrochimica Acta*, vol. 121, 1995, pp. 31-40.

Davis, G., "Electrochemical Techniques for the Development of Amperometric Biosensors", *Biosensors*, vol. 1, 1985, pp. 161-178.

Degani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", *The Journal of Physical Chemistry*, vol. 91, No. 6, 1987, pp. 1285-1289.

Degani, Y., et al., "Direct Electrical Communication Between Chemically Modified Enzymes and Metal Electrodes. 2. Methods for Bonding Electron-Transfer Relays to Glucose Oxidase and D-Amino-Acid Oxidase", *Journal of the American Chemical Society*, vol. 110, No. 8, 1988, pp. 2615-2620.

Degani, Y., et al., "Electrical Communication Between Redox Centers of Glucose Oxidase and Electrodes via Electrostatically and Covalently Bound Redox Polymers", *Journal of the American Chemical Society*, vol. 111, 1989, pp. 2357-2358.

Denisevich, P., et al., "Unidirectional Current Flow and Charge State Trapping at Redox Polymer Interfaces on Bilayer Electrodes: Principles, Experimental Demonstration, and Theory", *Journal of the American Chemical Society*, vol. 103, 1981, pp. 4727-4737.

Dicks, J. M., et al., "Ferrocene Modified Polypyrrole with Immobilised Glucose Oxidase and its Application in Amperometric Glucose Microbiosensors", *Annales de Biologie Clinique*, vol. 47, 1989, pp. 607-619.

Ellis, C. D., et al., "Selectivity and Directed Charge Transfer through an Electroactive Metallopolymer Film", *Journal of the American Chemical Society*, vol. 103, No. 25, 1981, pp. 7480-7483.

Engstrom, R. C., "Electrochemical Pretreatment of Glassy Carbon Electrodes", *Analytical Chemistry*, vol. 54, No. 13, 1982, pp. 2310-2314.

Engstrom, R. C., et al., "Characterization of Electrochemically Pretreated Glassy Carbon Electrodes", *Analytical Chemistry*, vol. 56, No. 2, 1984, pp. 136-141.

Feldman, B., et al., "Electron Transfer Kinetics at Redox Polymer/Solution Interfaces Using Microelectrodes and Twin Electrode Thin Layer Cells", *Journal of ElectroAnalytical Chemistry*, vol. 194, 1985, pp. 63-81.

Fischer, H., et al., "Intramolecular Electron Transfer Medicated by 4,4'-Bypyridine and Related Bridging Groups", *Journal of the American Chemical Society*, vol. 98, No. 18, 1976, pp. 5512-5517.

Foulds, N. C., et al., "Enzyme Entrapment in Electrically Conducting Polymers: Immobilisation of Glucose Oxidase in Polypyrrole and its Application in Amperometric Glucose Sensors", *Journal of the Chemical Society, Faraday Transactions 1*, vol. 82, 1986, pp. 1259-1264.

Foulds, N. C., et al , "Immobilization of Glucose Oxidase in Ferrocene-Modified Pyrrole Polymers", *Analytical Chemistry*, vol. 60, No. 22, 1988, pp. 2473-2478.

Frew, J. E., et al., "Electron-Transfer Biosensors", *Philosophical Transactions of The Royal Society of London*, vol. 316, 1987, pp. 95-106.

Gorton, L., et al., "Selective Detection in Flow Analysis Based on the Combination of Immobilized Enzymes and Chemically Modified Electrodes", *Analytica Chimica Acta*, vol. 250, 1991, pp. 203-248.

Gregg, B. A., et al., "Cross-Linked Redox Gels Containing Glucose Oxidase for Amperometric Bionsensor Applications", *Analytical Chemistry*, vol. 62, No. 3, 1990, pp. 258-263.

Gregg, B. A., et al., "Redox Polymer Films Containing Enzymes. 1. A Redox-Conducting Epoxy Cement: Synthesis, Characterization, and Electrocatalytic Oxidation of Hydroquinone", *Journal of Physical Chemistry*, vol. 95, No. 15, 1991, 5970-5975.

Hale, P. D., et al., "A New Class of Amperometric Biosensor Incorporating a Polymeric Electron-Transfer Mediator", *Journal of the American Chemical Society*, vol. 111, No. 9, 1989, pp. 3482-3484.

Harrison, D. J., et al., "Characterization of Perfluorosulfonic Acid Polymer Coated Enzyme Electrodes and a Miniatureized Integrated Potentiostat for Glucose Analysis in Whole Blood", *Analytical Chemistry*, vol. 60, No. 19, 1988, pp. 2002-2007.

Hawkridge, F. M., et al., "Indirect Coulometric Titration of Biological Electron Transport Components", *Analytical Chemistry*, vol. 45, No. 7, 1973, pp. 1021-1027.

Heller, A., "Electrical Connection Enzyme Redox Centers to Electrodes", *Journal of Physical Chemistry*, vol. 96, No. 9, 1990, pp. 3579-3587.

Heller, A., "Electrical Wiring of Redox Enzymes", *Accounts of Chemical Research* vol. 23, No. 5, 1990, 128-134.

Heller, A., et al., "Amperometric Biosensors Based on Three-Dimensional Hydrogel-Forming Epoxy Networks", *Sensors and Actuators B*, vol. 13-14, 1993, pp. 180-183.

Ianniello, R. M., et al., "Differential Pulse Voltammetric Study of Direct Electron Transfer in Glucose Oxidase Chemically Modified Graphite Electrodes", *Analytical Chemistry*, vol. 54, No. 7, 1982, pp. 1098-1101.

Ianniello, R. M., et al , "Immobilized Enzyme Chemically Modified Electrode as an Amperometric Sensor", *Analytical Chemistry*, vol. 53, No. 13, 1981, pp. 2090-2095.

Ikeda, T., et al., "Glucose Oxidase-Immobilized Benzoquinone-Carbon Paste Electrode as a Glucose Sensor", *Agricultural and Biological Chemistry*, vol. 49, No. 2, 1985, pp. 541-543.

Ikeda, T., et al., "Kinetics of Outer-Sphere Electron Transfers Between Metal Complexes in Solutions and Polymeric Films on Modified Electrodes", *Journal of the American Chemical Society*, vol. 103, No. 25, 1981, pp. 7422-7425.

Johnson, J. M., et al., "Potential-Dependent Enzymatic Activity in an Enzyme Thin-Layer Cell", *Analytical Chemistry*, vol. 54, No. 8, 1982, pp. 1377-1383.

Johnson, K. W., "Reproducible Electrodeposition of Biomolecules for the Fabrication of Miniature Electroenzymatic Biosensors", *Sensors and Actuators B*, vol. 5, 1991, pp. 85-89.

Jonsson, G., et al., "An Amperometric Glucose Sensor Made by Modification of a Graphite Electrode Surface With Immobilized Glucose Oxidase and Adsorbed Mediator", *Biosensors*, vol. 1, 1985, pp. 355-368.

Josowicz, M., et al., "Electrochemical Pretreatment of Thin Film Platinum Electrodes", *Journal of the Electrochemical Society*, vol. 135 No. 1, 1988, pp. 112-115.

Katakis, I., et al., "Electrostatic Control of the Electron Transfer Enabling Binding of Recombinant Glucose Oxidase and Redox Polyelectrolytes", *Journal of the American Chemical Society*, vol. 116, No. 8, 1994, pp. 3617-3618.

Katakis, I., et al., "L-α-Glycerophosphate and L-Lactate Electrodes Based on the Electrochemical 'Wiring' of Oxidases", *Analytical Chemistry*, vol. 64, No. 9, 1992, pp. 1008-1013.

Kenausis, G., et al., "'Wiring' of Glucose Oxidase and Lactate Oxidase Within a Hydrogel Made with Poly(vinyl pyridine) complexed with $[Os(4,4'-dimethoxy-2,2'-bipyridine)_2Cl]^{+/2+}$", *Journal of the Chemical Society, Faraday Transactions*, vol. 92, No. 20, 1996, pp. 4131-4136.

Koudelka, M., et al., "In-Vivo Behaviour of Hypodermically Implanted Microfabricated Glucose Sensors", *Biosensors & Bioelectronics*, vol. 6, 1991, pp. 31-36.

Kulys, J., et al., "Mediatorless Peroxidase Electrode and Preparation of Bienzyme Sensors", *Bioelectrochemistry and Bioenergetics*, vol. 24, 1990, pp. 305-311.

Lager, W., et al., "Implantable Electrocatalytic Glucose Sensor", *Hormone Metabolic Research*, vol. 26, 1994, pp. 526-530.

Lindner, E., et al., "Flexible (Kapton-Based) Microsensor Arrays of High Stability for Cardiovascular Applications", *Journal of the Chemical Society, Faraday Transactions*, vol. 89, No. 2, 1993, pp. 361-367.

Maidan, R., et al., "Elimination of Electrooxidizable Interferant-Produced Currents in Amperometric Biosensors", *Analytical Chemistry*, vol. 64, No. 23, 1992, pp. 2889-2896.

Mastrototaro, J. J., et al., "An Electroenzymatic Glucose Sensor Fabricated on a Flexible Substrate", *Sensors and Actuators B*, vol. 5, 1991, pp. 139-144.

McNeil, C. J., et al., "Thermostable Reduced Nicotinamide Adenine Dinucleotide Oxidase: Application to Amperometric Assay", *Analytical Chemistry*, vol. 61, No. 1, 1989, pp. 25-29.

Miyawaki, O., et al., "Electrochemical and Glucose Oxidase Coenzyme Activity of Flavin Adenine Dinucleotide Covalently Attached to Glassy Carbon at the Adenine Amino Group", *Biochimica et Biophysica Acta*, vol. 838, 1985, pp. 60-68.

Moatti-Sirat, D., et al., "Evaluating in Vitro and in Vivo the Interference of Ascorbate and Acetaminophen on Glucose Detection by a Needle-Type Glucose Sensor", *Biosensors & Bioelectronics*, vol. 7, 1992, pp. 345-352.

Moatti-Sirat, D., et al., "Reduction of Acetaminophen Interference in Glucose Sensors by a Composite Nafion Membrane: Demonstration in Rats and Man", *Diabetologia*, vol. 37, 1994, pp. 610-616.

Moatti-Sirat, D., et al., "Towards Continuous Glucose Monitoring: In Vivo Evaluation of a Miniaturized Glucose Sensor Implanted for Several Days in Rat Subcutaneous Tissue", *Diabetologia*, vol. 35, 1992, pp. 224-330.

Nagy, G., et al., "A New Type of Enzyme Electrode: The Ascorbic Acid Eliminator Electrode", *Life Sciences*, vol. 31, No. 23, 1982, pp. 2611-2616.

Nakamura, S., et al., "Effect of Periodate Oxidation on the Structure and Properties of Glucose Oxidase", *Biochimica et Biophysica Acta.*, vol. 445, 1976, pp. 294-308.

Narasimham, K., et al., "p-Benzoquinone Activation of Metal Oxide Electrodes for Attachment of Enzymes", *Enzyme and Microbial Technology*, vol. 7, 1985, pp. 283-286.

Ohara, T. J., "Osmium Bipyridyl Redox Polymers Used in Enzyme Electrodes", *Platinum Metals Review*, vol. 39, No. 2, 1995, pp. 54-62.

Ohara, T. J., et al., "'Wired' Enzyme Electrodes for Amperometric Determination of Glucose or Lactate in the Presence of Interfering Substances", *Analytical Chemistry*, vol. 66, No. 15, 1994, pp. 2451-2457.

Ohara, T. J., et al., "Glucose Electrodes Based on Cross-Linked $[Os(bpy)_2Cl]^{+/2+}$ $Complexed$ $Poly(1-Vinylimidazole)$ $Films$", *Analytical Chemistry*, vol. 65, No. 23, 1993, pp. 3512-3517.

Olievier, C. N., et al., "In Vivo Measurement of Carbon Dioxide Tension with a Miniature Electrodes", *Pflugers Archiv: European Journal of Physiology*, vol. 373, 1978, pp. 269-272.

Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", *Journal of ElectroAnalytical Chemistry*, vol. 260, 1989, pp. 487-494.

Palleschi, G., et al., "A Study of Interferences in Glucose Measurements in Blood by Hydrogen Peroxide Based Glucose Probes", *Analytical Biochemistry*, vol. 159, 1986, pp. 114-121.

Pankratov, I., et al., "Sol-Gel Derived Renewable-Surface Biosensors", *Journal of ElectroAnalytical Chemistry*, vol. 393, 1995, pp. 35-41.

Pathak, C., et al., "Rapid Photopolymerization of Immunoprotective Gels in Contact with Cells and Tissue", *Journal of the American Chemical Society*, vol. 114, No. 21, 1992, pp. 8311-8312.

Pickup, J., "Developing Glucose Sensors for in Vivo Use", *Tibtech*, vol. 11, 1993, pp. 285-291.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pickup, J., et al., "Potentially-Implantable, Amperometric Glucose Sensors with Mediated Electron Transfer: Improving the Operating Stability", *Biosensors*, vol. 4, 1989, pp. 109-119.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Poitout, V., et al., "A Glucose Monitoring System for on Line Estimation in Man of Blood Glucose Concentration Using a Miniaturized Glucose Sensor Implanted in the Subcutaneous Tissue and a Wearable Control Unit", *Diabetolgia*, vol. 36, 1993, pp. 658-663.

Poitout, V., et al., "Calibration in Dogs of a Subcutaneous Miniaturized Glucose Sensor Using a Glucose Meter for Blood Glucose Determination", *Biosensors & Bioelectronics*, vol. 7, 1992, pp. 587-592.

Poitout, V., et al., "In Vitro and in Vivo Evaluation in Dogs of a Miniaturized Glucose Sensor", *ASAIO Transactions*, vol. 37, No. 3, 1991, pp. M298-M300.

Pollak, A., et al., "Enzyme Immobilization by Condensation Copolymerization into Cross-Linked Polyacrylamide Gels", *Journal of the American Chemical Society*, vol. 102, No. 20, 1980, pp. 6324-6336.

Reach, G., et al., "Can Continuous Glucose Monitoring Be Used for the Treatment of Diabetes?", *Analytical Chemistry*, vol. 64, No. 6, 1992, pp. 381-386.

Rebrin, K., et al., "Automated Feedback Control of Subcutaneous Glucose Concentration in Diabetic Dogs", *Diabetologia*, vol. 32, 1989, pp. 573-576.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Samuels, G. J., et al., "An Electrode-Supported Oxidation Catalyst Based on Ruthenium (IV). pH 'Encapsulation' in a Polymer Film", *Journal of the American Chemical Society*, vol. 103, No. 2, 1981, pp. 307-312.

Sasso, S. V., et al., "Electropolymerized 1,2-Diaminobenzene as a Means to Prevent Interferences and Fouling and to Stabilize Immobilized Enzyme in Electrochemical Biosensors", *Analytical Chemistry*, vol. 62, No. 11, 1990, pp. 1111-1117.

Scheller, F., et al., "Enzyme Electrodes and Their Application", *Philosophical Transactions of The Royal Society of London B*, vol. 316, 1987, pp. 85-94.

Schmehl, R. H., et al., "The Effect of Redox Site Concentration on the Rate of Mediated Oxidation of Solution Substrates by a Redox Copolymer Film", *Journal of ElectroAnalytical Chemistry*, vol. 152, 1983, pp. 97-109.

Shichiri, M., et al., "Glycaemic Control in Pancreatectomized Dogs with a Wearable Artificial Endocrine Pancreas", *Diabetologia*, vol. 24, 1983, pp. 179-184.

Sittampalam, G., et al., "Surface-Modified Electrochemical Detector for Liquid Chromatography", *Analytical Chemistry*, vol. 55, No. 9, 1983, pp. 1608-1610.

Soegijoko, S., et al., "External Artificial Pancreas: A New Control Unit Using Microprocessor", *Hormone and Metabolic Research Supplement Series*, vol. 12, 1982, pp. 165-169.

Sprules, S. D., et al., "Evaluation of a New Disposable Screen-Printed Sensor Strip for the Measurement of NADH and Its Modification to Produce a Lactate Biosensor Employing Microliter Volumes", *Electroanalysis*, vol. 8, No. 6, 1996, pp. 539-543.

Sternberg, F., et al., "Calibration Problems of Subcutaneous Glucosensors when Applied 'In-Situ' in Man", *Hormone and Metabolic Research*, vol. 26, 1994, pp. 523-526.

Sternberg, R., et al., "Covalent Enzyme Coupling on Cellulose Acetate Membranes for Glucose Sensor Development", *Analytical Chemistry*, vol. 60, No. 24, 1988, pp. 2781-2786.

Sternberg, R., et al., "Study and Development of Multilayer Needle-Type Enzyme-Based Glucose Microsensors", *Biosensors*, vol. 4, 1988, pp. 27-40.

Suekane, M., "Immobilization of Glucose Isomerase", *Zettschrift fur Allgemeine Mikrobiologie*, vol. 22, No. 8, 1982, pp. 565-576.

Tajima, S., et al., "Simultaneous Determination of Glucose and 1,5-Anydroglucitol", *Chemical Abstracts*, vol. 111, No. 25, 1989, pp. 394.

Tarasevich, M. R., "Bioelectrocatalysis", *Comprehensive Treatise of Electrochemistry*, vol. 10, 1985, pp. 231-295.

Tatsuma, T., et al., "Enzyme Monolayer- and Bilayer-Modified Tin Oxide Electrodes for the Peroxide and Glucose", *Analytical Chemistry*, vol. 61, No. 21, 1989, pp. 2352-2355.

Taylor, C., et al., "'Wiring' of Glucose Oxidase Within a Hydrogel Made with Polyvinyl Imidazole Complexed with [(Os-4,4'-dimethoxy-2,2'-bipyridine)C1]$^{+/2+}$", *Journal of ElectroAnalytical Chemistry*, vol. 396, 1995, pp. 511-515.

Trojanowicz, M., et al., "Enzyme Entrapped Polypyrrole Modified Electrode for Flow-Injection Determination of Glucose", *Biosensors & Bioelectronics*, vol. 5, 1990, pp. 149-156.

Turner, A., et al., "Diabetes Mellitus: Biosensors for Research and Management", *Biosensors*, vol. 1, 1985, pp. 85-115.

Turner, R. F., et al., "A Biocompatible Enzyme Electrode for Continuous in vivo Glucose Monitoring in Whole Blood", *Sensors and Actuators B*, vol. 1, 1990, pp. 561-564.

Tuzhi, P., et al., "Constant Potential Pretreatment of Carbon Fiber Electrodes for in Vivo Electrochemistry", *Analytical Letters*, vol. 24, No. 6, 1991, pp. 935-945.

Umana, M., "Protein-Modified Electrochemically Active Biomaterial Surface", *U.S. Army Research Office, Analytical Letters*, vol. 24, No. 6, 1991, pp. 935-945.

Urban, G., et al., "Miniaturized Thin-Film Biosensors Using Covalently Immobilized Glucose Oxidase", *Biosensors & Bioelectronics*, vol. 6, 1991, pp. 555-562.

Velho, G., et al., "In Vitro and in Vivo Stability of Electrode Potentials in Needle-Type Glucose Sensors", *Diabetes*, vol. 38, No. 2, 1989, pp. 164-171.

Velho, G., et al., "Strategies for Calibrating a Subcutaneous Glucose Sensor", *Biomedica Biochimica Acta*, vol. 48, 1989, pp. 957-964.

Von Woedtke, T., et al., "In Situ Calibration of Implanted Electrochemical Glucose Sensors", *Biomedica Biochimica Acta*, vol. 48, 1989, pp. 943-952.

Vreeke, M. S., et al., "Hydrogen Peroxide Electrodes Based on Electrical Connection of Redox Centers of Various Peroxidases to Electrodes through a Three-Dimensional Electron-Relaying Polymer Network", *Diagnostic Biosensors Polymers, Chapter 15*, 1993, pp. 180-193.

Vreeke, M., et al., "Hydrogen Peroxide and γ-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", *Analytical Chemistry*, vol. 64, No. 24, 1992, pp. 3084-3090.

Wang, D. L., et al., "Miniaturized Flexible Amperometric Lactate Probe", *Analytical Chemistry*, vol. 65, No. 8, 1993, pp. 1069-1073.

Wang, J., et al., "Activation of Glassy Carbon Electrodes by Alternating Current Electrochemical Treatment", *Analytica Chimica Acta*, vol. 167, 1985, pp. 325-334.

Wang, J., et al., "Amperometric Biosensing of Organic Peroxides with Peroxidase-Modified Electrodes", *Analytica Chimica Acta*, vol. 254, 1991, pp. 81-88.

Wang, J., et al., "Screen-Printable Sol-Gel Enzyme-Containing Carbon Inks", *Analytical Chemistry*, vol. 68, No. 15, 1996, pp. 2705-2708.

Wang, J., et al., "Sol-Gel-Derived Metal-Dispersed Carbon Composite Amperometric Biosensors", *Electroanalysis*, vol. 9, No. 1, 1997, pp. 52-55.

Williams, D. L., et al., "Electrochemical-Enzymatic Analysis of Blood Glucose and Lactate", *Analytical Chemistry*, vol. 42, No. 1, 1970, pp. 118-121.

Wilson, G. S., et al., "Progress Toward the Development of an Implantable Sensor for Glucose", *Clinical Chemistry*, vol. 38, No. 9, 1992, pp. 1613-1617.

Yabuki, S., et al., "Electro-Conductive Enzyme Membrane", *Journal of the Chemical Society*, 1989, pp. 945-946.

Yang, L., et al., "Determination of Oxidase Enzyme Substrates Using Cross-Flow Thin-Layer Amperometry", *Electroanalysis*, vol. 8, No. 8-9, 1996, pp. 716-721.

Yao, S. J., et al., "The Interference of Ascorbate and Urea in Low-Potential Electrochemical Glucose Sensing", *Proceedings of the Twelfth Annual International Conference of the IEEE Engineering in Medicine and Biology Society*, vol. 12, Part 2, 1990, pp. 487-489.

Yao, T., "A Chemically-Modified Enzyme Membrane Electrode as an Amperometric Glucose Sensor", *Analytica Chimica Acta*, vol. 148, 1983, pp. 27-33.

Ye, L., et al., "High Current Density 'Wired' Quinoprotein Glucose Dehydrogenase Electrode", *Analytical Chemistry*, vol. 65, No. 3, 1993, pp. 238-241.

Yildiz, A., et al., "Evaluation of an Improved Thin-Layer Electrode", *Analytical Chemistry*, vol. 40, No. 7, 1968, pp. 1018-1024.

Zamzow, K., et al., "New Wearable Continuous Blood Glucose Monitor (BGM) and Artificial Pancreas (AP)", *Diabetes*, vol. 39, 1990, pp. 5A-20.

Zhang, Y., et al., "Application of Cell Culture Toxicity Tests to the Development of Implantable Biosensors", *Biosensors & Bioelectronics*, vol. 6, 1991, pp. 653-661.

Zhang, Y., et al., "Elimination of the Acetaminophen Interference in an Implantable Glucose Sensor", *Analytical Chemistry*, vol. 66, No. 7, 1994, pp. 1183-1188.

Morff, et al., "Microfabrication of Reproducible, Economical, Electroenzymatic Glucose Sensors", *Annual International Conference of the IEEE Engineering in Medicine and Biology Society*, vol. 12, No. 2, 1990, pp. 0483-0484.

Teng, et al., "A Microprocessor-Controlled Ink Jet Printing System for Electronic Circuits", *I.E.E.E. Transactions on Industrial Electronics*, vol. 35, No. 3, 1988, pp. 407-412.

European Patent Application No. 10012412.2, Extended European Search Report, mailed Apr. 21, 2011.

European Patent Application No. 10012411.4, Extended European Search Report, mailed Feb. 22, 2011.
Bowyer, W. J., et al., "Electrochemical Measurements in Submicroliter Volumes", *Analytical Chemistry*, vol. 64, No. 4, 1992, pp. 459-462.
Bratten, C. D. T., et al., "Micromachining Sensors for Electrochemical Measurement in Subnanoliter Volumes", *Analytical Chemistry*, vol. 69, No. 2, 1997, pp. 253-258.
Karube, I., et al., "Microbiosensors Prepared by Micromachining", *Biosensors: Fundamentals, Technologies and Applications*, 1992, pp. 478-489.
Koudelka, M., et al., "Planar Amperometric Enzyme-Based Glucose Microelectrode", *Sensors and Actuators*, vol. 18, 1989, pp. 157-165.
Niwa, O., et al., "Concentration of Extracellular L-Glutamate Released from Cultured Nerve Cells Measured with a Small-Volume Online Sensor", *Analytical Chemistry*, vol. 68, No. 11, 1996, pp. 1865-1870.
Takata, Y., "Chapter 4: Liquid Chromatography with Coulometric Detector", *Advances in Liquid Chromatography*, 1996, pp. 43-74.
European Patent Application No. 99 908 338.9, Office Action mailed Oct. 8, 2007.
Japanese Patent Application No. 2000-534863, English Translation & Original Language of Office Action mailed Oct. 20, 2009.
Japanese Patent Application No. 2000-534863, English Translation of Office Action mailed Aug. 23, 2010.
Japanese Patent Application No. 2000-534863, English Translation of Office Action mailed Feb. 3, 2009.
PCT Application No. PCT/US1999/003781, First Written Opinion mailed Dec. 9, 1999.
PCT Application No. PCT/US1999/003781, International Search Report mailed Feb. 8, 1999.
PCT Application No. PCT/US1999/003781, Second Written Opinion mailed Mar. 31, 2000.
U.S. Appl. No. 09/034,422, Notice of Allowance mailed Jan. 18, 2000.
U.S. Appl. No. 09/034,422, Supplemental Notice of Allowance mailed May 24, 2000.
U.S. Appl. No. 10/405,765, Advisory Action mailed Oct. 26, 2004.
U.S. Appl. No. 10/405,765, Notice of Allowance mailed Jan. 27, 2005.
U.S. Appl. No. 10/405,765, Office Action mailed Aug. 5, 2004.
U.S. Appl. No. 10/405,765, Office Action mailed Mar. 19, 2004.
U.S. Appl. No. 11/204,551, Notice of Allowance mailed Mar. 17, 2008.
U.S. Appl. No. 11/204,551, Notice of Allowance mailed Mar. 3, 2010.
U.S. Appl. No. 11/204,551, Office Action mailed Apr. 8, 2008.
U.S. Appl. No. 11/204,551, Office Action mailed Jun. 3, 2008.
U.S. Appl. No. 11/204,551, Office Action mailed Jun. 5, 2007.
U.S. Appl. No. 11/204,551, Office Action mailed Mar. 5, 2009.
U.S. Appl. No. 11/204,551, Office Action mailed Nov. 15, 2007.
U.S. Appl. No. 11/929,906, Office Action mailed Feb. 23, 2010.
U.S. Appl. No. 11/929,906, Office Action mailed Oct. 28, 2010.
U.S. Appl. No. 11/929,945, Office Action mailed Dec. 11, 2009.
U.S. Appl. No. 11/929,945, Office Action mailed Mar. 2, 2011.
U.S. Appl. No. 11/929,945, Office Action mailed May 4, 2009.
U.S. Appl. No. 11/929,945, Office Action mailed Sep. 15, 2008.
U.S. Appl. No. 11/929,952, Office Action mailed Mar. 5, 2010.
U.S. Appl. No. 11/929,952, Office Action mailed Oct. 25, 2010.
U.S. Appl. No. 11/929,959, Notice of Allowance Mailed Aug. 24, 2010.
U.S. Appl. No. 11/929,959, Notice of Allowance Mailed Oct. 21, 2010.
U.S. Appl. No. 11/929,959, Office Action mailed Jul. 14, 2009.
U.S. Appl. No. 11/929,959, Office Action mailed Jun. 7, 2010.
U.S. Appl. No. 11/929,964, Notice of Allowance mailed Jun. 9, 2010.
U.S. Appl. No. 11/929,964, Office Action mailed Feb. 18, 2010.
U.S. Appl. No. 11/929,964, Office Action mailed Jul. 13, 2009.
U.S. Appl. No. 11/929,967, Office Action mailed Mar. 9, 2010.
U.S. Appl. No. 11/929,967, Office Action mailed Oct. 29, 2010.
U.S. Appl. No. 11/929,986, Notice of Allowance mailed Nov. 5, 2010.
U.S. Appl. No. 11/929,986, Office Action mailed Mar. 11, 2010.
U.S. Appl. No. 11/929,994, Office Action mailed Jan. 14, 2010.
U.S. Appl. No. 11/929,994, Office Action mailed Jul. 1, 2009.
U.S. Appl. No. 11/930,004, Office Action mailed Apr. 7, 2011.
U.S. Appl. No. 11/930,004, Office Action mailed Aug. 24, 2009.
U.S. Appl. No. 11/930,004, Office Action mailed Feb. 18, 2010.
U.S. Appl. No. 11/930,011, Advisory Action mailed Dec. 17, 2009.
U.S. Appl. No. 11/930,011, Office Action mailed Dec. 16, 2008.
U.S. Appl. No. 11/930,011, Office Action mailed Feb. 24, 2010.
U.S. Appl. No. 11/930,011, Office Action mailed Jul. 23, 2010.
U.S. Appl. No. 11/930,011, Office Action mailed Oct. 9, 2010.
U.S. Appl. No. 11/930,011, Supplemental Office Action mailed Aug. 26, 2010.
U.S. Appl. No. 90/007,913, Request for Reexamination of U.S. Patent No. 6,284,478, filed Feb. 1, 2006.
U.S. Appl. No. 90/007,914, Request for Reexamination of U.S. Patent No. 6,329,161, filed Feb. 1, 2006.
U.S. Appl. No. 90/008,173, Request for Reexamination of U.S. Patent No. 6,134,461, filed Aug. 16, 2006.
U.S. Appl. No. 90/008,457, Request for Reexamination of U.S. Patent No. 6,990,366 filed Jan. 23, 2007.
U.S. Appl. No. 90/008,665, Request for Reexamination of U.S. Patent No. 6,284,478, filed May 25, 2007.
U.S. Appl. No. 90/008,713, Request for Reexamination of U.S. Patent No. 6,329,161, filed Jul. 25, 2007.
U.S. Appl. No. 90/008,928, Request for Reexamination of U.S. Patent No. 6,134,461, filed Nov. 16, 2007.
U.S. Appl. No. 90/009,104, Request for Reexamination of U.S. Patent No. 6,990,366 filed Apr. 8, 2008.
U.S. Appl. No. 90/009,270, Request for Reexamination of U.S. Patent No. 6,175,752 filed Sep. 8, 2008.
U.S. Appl. No. 90/009,279, Request for Reexamination of U.S. Patent No. 6,565,509 filed Sep. 17, 2008.
U.S. Appl. No. 90/009,328, Request for Reexamination of U.S. Patent No. 6,990,366 filed Nov. 10, 2008.
U.S. Appl. No. 90/009,390, Request for Reexamination of U.S. Patent No. 6,565,509 filed Jan. 21, 2009.
U.S. Appl. No. 90/009,472, Replacement Request for Reexamination of U.S. Patent No. 6,284,478 filed Sep. 3, 2009.
U.S. Appl. No. 90/009,472, Request for Reexamination of U.S. Patent No. 6,284,478 filed May 27, 2009.
U.S. Appl. No. 90/009,488, Replacement Request for Reexamination of U.S. Patent No. 6,329,161 filed Jul. 31, 2009.
U.S. Appl. No. 90/009,488, Request for Reexamination of U.S. Patent No. 6,329,161 filed Jun. 10, 2009.
U.S. Appl. No. 90/009,497, Request for Reexamination of U.S. Patent No. 6,175,752 filed Jun. 17, 2009.
U.S. Appl. No. 90/009,620, Request for Reexamination of U.S. Patent No. 6,329,161 filed Oct. 27, 2009.
U.S. Appl. No. 90/009,763, Request for Reexamination of U.S. Patent No. 6,134,461, filed Jun. 18, 2010.
U.S. Appl. No. 90/010,791, Request for Reexamination of U.S. Patent No. 6,990,366 filed Dec. 22, 2009.
U.S. Appl. No. 90/010,835, Request for Reexamination of U.S. Patent No. 6,134,461, filed Jan. 27, 2010.
U.S. Appl. No. 90/011,317, Corrected Request for Reexamination of U.S. Patent No. 6,484,046, filed Jan. 14, 2011.
U.S. Appl. No. 90/011,317, Order Granting Request for Reexamination of U.S. Patent No. 6,484,046, mailed Feb. 18, 2011.
U.S. Appl. No. 90/011,317, Request for Reexamination of U.S. Patent No. 6,484,046, filed Nov. 5, 2010.
U.S. Appl. No. 90/011,346, Order Granting Request for Reexamination of U.S. Patent No. 6,103,033, mailed Feb. 17, 2011.
U.S. Appl. No. 90/011,346, Request for Reexamination of U.S. Patent No. 6,103,033, filed Nov. 19, 2010.
Gamache, et al., "Simultaneous Measurement of Monoamines, Metabolites and Amino Acids in Brain Tissue and Microdialysis Perfusates", *Journal of Chromatrography*, vol. 614, 1993, pp. 213-220.
Nakabayashi, Y., et al., "Evaluation of Osmium(II) Complexes as Electron Transfer Mediators Accessible for Amperometric Glucose Sensors", *Analytical Sciences*, vol. 17, 2001, pp. 945-950.

Zhang, Y., et al., "Evaluation of Substituted-1,10-Phenanthroline Complexes of Osmium as Mediator for Glucose Oxidase of *Aspergiullus niger*", *Analytica Chimica Acta*, vol. 408, 2000, pp. 225-232.

U.S. Appl. No. 11/929,906, Office Action mailed Sep. 2, 2011.

U.S. Appl. No. 11/929,945, Notice of Allowance mailed Nov. 28, 2011.

U.S. Appl. No. 11/929,952, Office Action mailed Sep. 7, 2011.

U.S. Appl. No. 11/929,967, Office Action mailed Sep. 7, 2011.

U.S. Appl. No. 90/011,730, Request for Reexamination of U.S. Patent No. 6,175,752 filed Jun. 3, 2011.

* cited by examiner

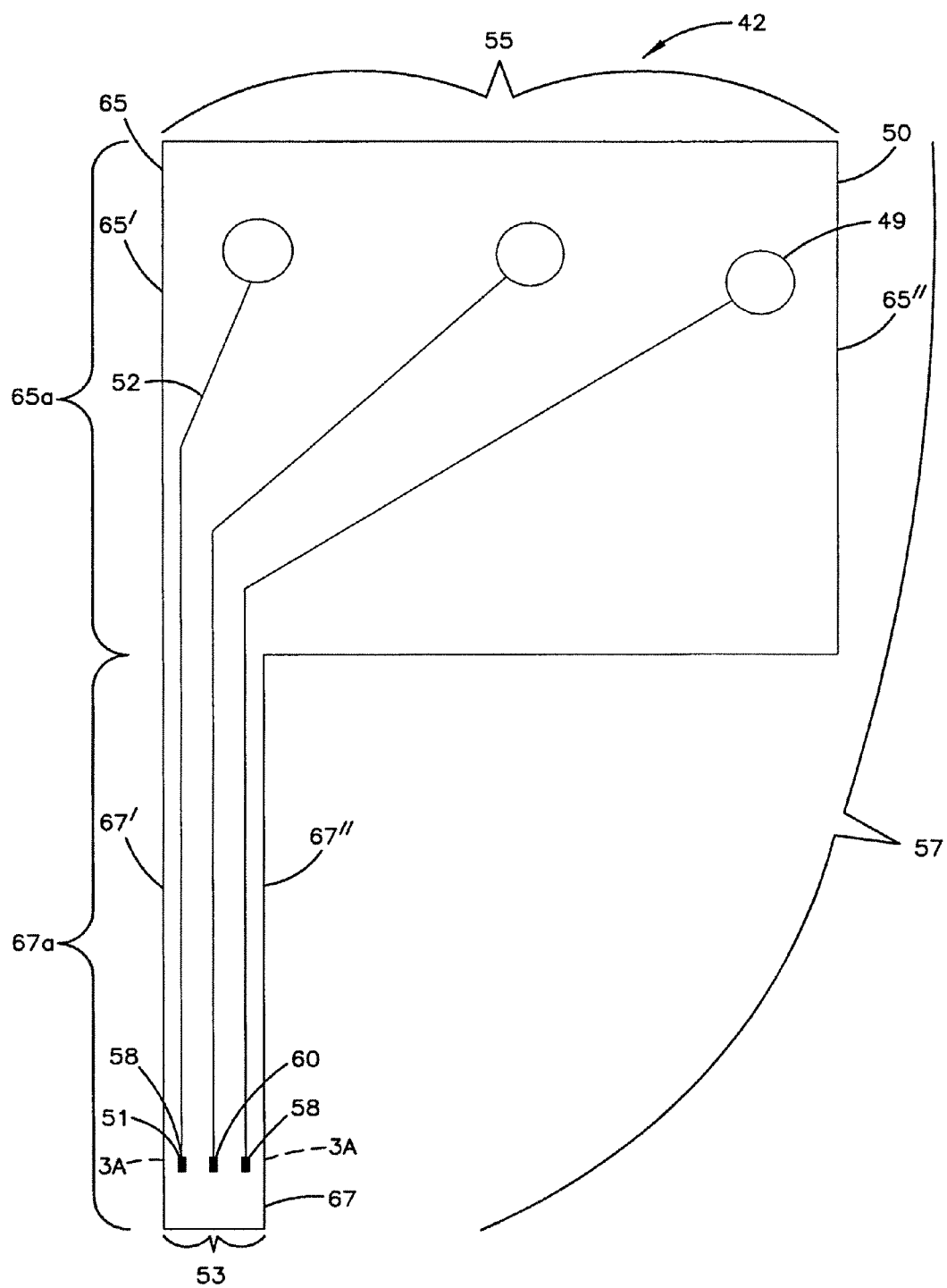

SENSOR FOR DETERMINATION OF GLUCOSE

RELATED APPLICATIONS

This application is a continuation of application Ser. No. 11/204,551 filed Aug. 16, 2005 now U.S. Pat. No. 7,721,412, which is a continuation of application Ser. No. 10/405,765 filed Mar. 31, 2003, now U.S. Pat. No. 6,973,706, which is a continuation of application Ser. No. 09/598,776, filed Jun. 16, 2000, abandoned, which is a continuation of application Ser. No. 09/034,422, filed Mar. 4, 1998, now U.S. Pat. No. 6,103,033, all of which are incorporated herein by reference.

FIELD OF THE INVENTION

The present invention relates to a process for the manufacture of small sensors, including small electrochemical sensors. More particularly, the process of the invention includes disposing a conductive material on a substrate, preferably in channels formed on the surface of the substrate, thereby forming conductive traces and electrodes in a rapid, efficient manner, with reproducible surface areas and conductivities, and particularly forming very small conductive traces.

BACKGROUND OF THE INVENTION

The monitoring of the level of glucose or other biochemicals, such as lactate, in individuals is often important. High or low levels of glucose or other biochemicals may be detrimental to an individual's health. The monitoring of glucose is particularly important to individuals with diabetes as they must determine when insulin is needed to reduce glucose levels in their bloodstream or when additional glucose is needed to raise the level of glucose in the bloodstream.

Conventional techniques for monitoring blood glucose levels currently include the periodic drawing of blood, the application of that blood to a test strip, and the determination of the blood glucose concentration using electrochemical, calorimetric, or photometric methods. This technique does not allow for continuous monitoring of blood glucose levels, but must be performed on a periodic basis.

A variety of other devices have also been developed for continuous monitoring of analytes in the blood stream or subcutaneous tissue. Many of these devices use electrochemical sensors which are directly implanted in a blood vessel or in the subcutaneous tissue of a user. However, these devices are often large, bulky, and/or inflexible and many can not be used effectively outside of a controlled medical facility, such as a hospital or a doctor's office, unless the user is restricted in his activities.

The user's comfort and the range of activities that can be performed while the sensor is implanted are important considerations in designing extended-use sensors for continuous in vivo monitoring of the level of an analyte, such as glucose. There is a need for a small, comfortable device which can continuously monitor the level of an analyte, such as glucose, while still permitting the user to engage in normal activities outside the boundaries of a controlled medical facility. There is also a need for methods that allow such small, comfortable devices to be relatively inexpensively, efficiently, reproducibly and precisely manufactured.

A significant problem in the manufacture of in vitro electrochemical sensors has been the inability to manufacture small electrodes with reproducible surfaces. Present techniques for printing or silk screening carbon electrodes onto substrates yield electrodes with poorly defined or irreproducible surface areas and conductivities, particularly at trace widths below 250 μm (10 mils).

Small sized non-electrochemical sensors including, for example, temperature probes, would also be useful if they could be reliably and reproducibly manufactured. A process for the manufacture of small sensors with reproducible surfaces is needed.

SUMMARY OF THE INVENTION

The present invention provides a process for the manufacture of small sensors which is efficient, reliable, and provides reproducible surfaces. The process of the invention includes forming one or more channels on a surface of a substrate and disposing a conductive material within the formed channels to form an electrode. Various embodiments of the process include the manufacture of electrochemical sensors by disposing a sensing layer on the conductive material within the formed channels; the manufacture of a sensor having one or more working electrodes; counter/reference electrodes, temperature sensors and the like formed in a plurality of channels on one or more surfaces of the substrate; and sensors having a plurality of electrode traces separated by very small distances to form a small electrochemical sensor.

One aspect of the present invention relates to a process for the manufacture of an electrochemical sensor using a web process, which may be continuous or non-continuous. The process includes the steps of providing a substrate web, and disposing a pattern of a conductive material on the continuous substrate web to form an electrode, including one or more working electrodes and counter electrodes. The method also includes the step of disposing a sensing layer on the working electrode disposed on the web. Such a continuous web process is adapted for relatively inexpensively, efficiently, reproducibly and precisely manufacturing electrochemical sensors.

Another aspect of the present invention includes a process for the manufacture of an electrochemical sensor having one or more working and/or counter electrodes disposed on a sensor substrate. The method includes the steps of providing a substrate and disposing a conductive material on the substrate to form one or more working electrodes and/or counter electrodes, and optionally disposing a sensing layer on the working electrode.

A further aspect of the present invention relates to process for the manufacture of an electrochemical sensor having electrodes and conductive traces disposed within channels defined by a sensor substrate. The process includes the steps of providing a substrate, and forming first and second channels in the substrate. The process also includes the step of disposing a conductive material within the channels to form a working electrode located at the first channel, and a counter electrode located at the second channel. The process further includes the optional step of disposing a sensing layer on the working electrode.

The invention includes a continuous process for multi-step preparation of sensors including the efficient and precise deposition of small electrode tracings; sensing layers; counter electrodes, temperature sensors, and like constituents to efficiently produce electrochemical and non-electrochemical biosensors.

The above summary of the present invention is not intended to describe each disclosed embodiment or every implementation of the present invention. The Figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 2 is a top view of one embodiment of an analyte sensor, according to the invention;

Figure 1:
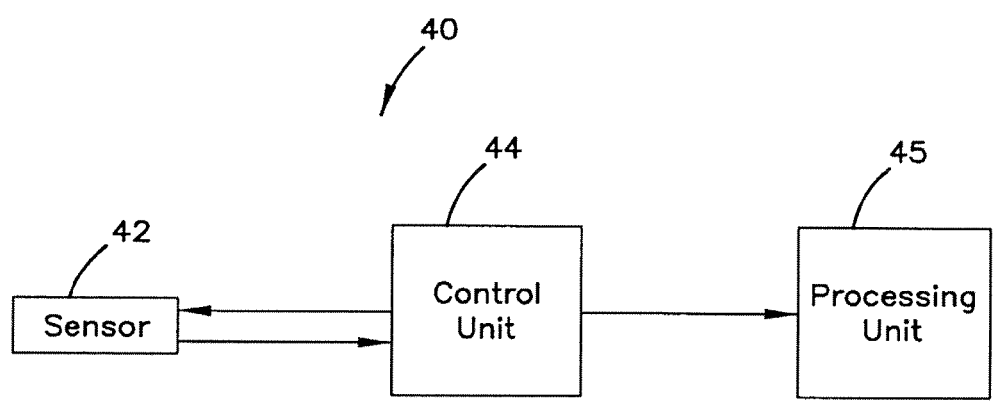
FIG. 1 is a block diagram of one embodiment of an analyte monitor using an analyte sensor, according to the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE PREFERRED EMBODIMENT

The process of the present invention is applicable to the manufacture of an analyte sensor for the in vivo and/or in vitro determination of an analyte, such as glucose or lactate, in a fluid. The process is also applicable to the production of other sensors, including, for example biosensors relaying a chemical signal through a conductive tracing.

The analyte sensors of the present invention can be utilized in a variety of contexts. For example, one embodiment of the analyte sensor is subcutaneously implanted in the interstitial tissue of a patient for the continuous or periodic monitoring of a level of an analyte in a patient's interstitial fluid. This can then be used to infer the analyte level in the patient's bloodstream. Other in vivo analyte sensors can be made, according to the invention, for insertion into a vein, artery, or other portion of the body containing fluid in order to measure a bioanalyte. The in vivo analyte sensors may be configured for obtaining a single measurement and/or for monitoring the level of the analyte over a time period which may range from hours to days or longer.

Another embodiment of the analyte sensor is used for the in vitro determination of the presence and/or level of an analyte in a sample, and, particularly, in a small volume sample (e.g., 1 to 10 microliters or less). While the present invention is not so limited, an appreciation of various aspects of the invention will be gained through a discussion of the examples provided below.

The following definitions are provided for terms used herein. A "counter electrode" refers to an electrode paired with the working electrode, through which passes a current equal in magnitude and opposite in sign to the current passing through the working electrode. In the context of the invention, the term "counter electrode" is meant to include counter electrodes which also function as reference electrodes (i.e., a counter/reference electrode).

An "electrochemical sensor" is a device configured to detect the presence and/or measure the level of an analyte in a sample via electrochemical oxidation and reduction reactions on the sensor. These reactions are transduced to an electrical signal that can be correlated to an amount, concentration, or level of an analyte in the sample.

"Electrolysis" is the electrooxidation or electroreduction of a compound either directly at an electrode or via one or more electron transfer agents.

A compound is "immobilized" on a surface when it is entrapped on or chemically bound to the surface.

A "non-leachable" or "non-releasable" compound or a compound that is "non-leachably disposed" is meant to define a compound that is affixed on the sensor such that it does not substantially diffuse away from the working surface of the working electrode for the period in which the sensor is used (e.g., the period in which the sensor is implanted in a patient or measuring a sample).

Components are "immobilized" within a sensor, for example, when the components are covalently, ionically, or coordinatively bound to constituents of the sensor and/or are entrapped in a polymeric or sol-gel matrix or membrane which precludes mobility.

An "electron transfer agent" is a compound that carries electrons between the analyte and the working electrode, either directly, or in cooperation with other electron transfer agents. One example of an electron transfer agent is a redox mediator.

A "working electrode" is an electrode at which the analyte (or a second compound whose level depends on the level of the analyte) is electrooxidized or electroreduced with or without the agency of an electron transfer agent.

A "working surface" is that portion of the working electrode which is coated with or is accessible to the electron transfer agent and configured for exposure to an analyte-containing fluid.

A "sensing layer" is a component of the sensor which includes constituents that facilitate the electrolysis of the analyte. The sensing layer may include constituents such as an electron transfer agent, a catalyst which catalyzes a reaction of the analyte to produce a response at the electrode, or both. In some embodiments of the sensor, the sensing layer is non-leachably disposed in proximity to or on the working electrode.

A "non-corroding" conductive material includes non-metallic materials, such as carbon and conductive polymers.

Analyte Sensor Systems

The sensors of the present invention can be utilized in a variety of devices and under a variety of conditions. The particular configuration of a sensor may depend on the use for which the sensor is intended and the conditions under which the sensor will operate (e.g., in vivo or in vitro). One embodiment of the analyte sensor is configured for implantation into a patient or user for in vivo operation. For example, implantation of the sensor may be made in the arterial or venous systems for direct testing of analyte levels in blood. Alternatively, a sensor may be implanted in the interstitial tissue for determining the analyte level in interstitial fluid. This level may be correlated and/or converted to analyte levels in blood or other fluids. The site and depth of implantation may affect the particular shape, components, and configuration of the sensor. Subcutaneous implantation may be preferred, in some cases, to limit the depth of implantation of the sensor. Sensors may also be implanted in other regions of the body to determine analyte levels in other fluids. Particularly useful sensors are described in U.S. Pat. No. 6,134,461, incorporated herein by reference.

An implantable analyte sensor may be used as part of an analyte monitoring system to continuously and/or periodically monitor the level of an analyte in a body fluid of a patient. In addition to the sensor 42, the analyte monitoring system 40 also typically includes a control unit 44 for operating the sensor 42 (e.g., providing a potential to the electrodes and obtaining measurements from the electrodes) and a processing unit 45 for analyzing the measurements from the sensor 42. The control unit 44 and processing unit 45 may be combined in a single unit or may be separate.

Another embodiment of the sensor may be used for in vitro measurement of a level of an analyte. The in vitro sensor is coupled to a control unit and/or a processing unit to form an analyte monitoring system. In some embodiments, an in vitro analyte monitoring system is also configured to provide a sample to the sensor. For example, the analyte monitoring system may be configured to draw a sample from, for example, a lanced wound using a wicking and/or capillary action. The sample may then be drawn into contact with the sensor. Examples of such sensors may be found in U.S. patent application Ser. No. 08/795,767 and PCT Patent Application Publication No. WO 98/35225, incorporated herein by reference.

Other methods for providing a sample to the sensor include using a pump, syringe, or other mechanism to draw a sample from a patient through tubing or the like either directly to the sensor or into a storage unit from which a sample is obtained for the sensor. The pump, syringe, or other mechanism may operate continuously, periodically, or when desired to obtain a sample for testing. Other useful devices for providing an analyte-containing fluid to the sensor include microfiltration and/or microdialysis devices. In some embodiments, particularly those using a microdialysis device, the analyte may be drawn from the body fluid through a microporous membrane, for example, by osmotic pressure, into a carrier fluid which is then conveyed to the sensor for analysis. Other useful devices for acquiring a sample are those that collect body fluids transported across the skin using techniques, such as reverse iontophoresis, to enhance the transport of fluid containing analyte across the skin.

The Sensor

A sensor 42, according to the invention, includes at least one working electrode 58 formed on a substrate 50, as shown in FIG. 2. The sensor 42 may also include at least one counter electrode 60 (or counter/reference electrode) and/or at least one reference electrode 62 (see FIG. 8). The counter electrode 60 and/or reference electrode 62 may be formed on the substrate 50 or may be separate units. For example, the counter electrode and/or reference electrode may be formed on a second substrate which is also implanted in the patient or, for some embodiments of the implantable sensors, the counter electrode and/or reference electrode may be placed on the skin of the patient with the working electrode or electrodes being implanted into the patient. The use of an on-the-skin counter and/or reference electrode with an implantable working electrode is described in U.S. Pat. No. 5,593,852, incorporated herein by reference.

The working electrode or electrodes 58 are formed using conductive traces 52 disposed on the substrate 50. The counter electrode 60 and/or reference electrode 62, as well as other optional portions of the sensor 42, such as a temperature probe 66 (see FIG. 8), may also be formed using conductive traces 52 disposed on the substrate 50. These conductive traces 52 may be formed over a smooth surface of the substrate 50 or within channels 54 formed by, for example, embossing, indenting or otherwise creating a depression in the substrate 50.

A sensing layer 64 (see FIGS. 3A and 3B) is often formed proximate to or on at least one of the working electrodes 58 to facilitate the electrochemical detection of the analyte and the determination of its level in the sample fluid, particularly if the analyte can not be electrolyzed at a desired rate and/or with a desired specificity on a bare electrode. The sensing layer 64 may include an electron transfer agent to transfer electrons directly or indirectly between the analyte and the working electrode 58. The sensing layer 64 may also contain a catalyst to catalyze a reaction of the analyte. The components of the sensing layer may be in a fluid or gel that is proximate to or in contact with the working electrode 58. Alternatively, the components of the sensing layer 64 may be disposed in a polymeric or sol-gel matrix that is proximate to or on the working electrode 58. Preferably, the components of the sensing layer 64 are non-leachably disposed within the sensor 42. More preferably, the components of the sensor 42 are immobilized within the sensor 42.

In addition to the electrodes 58, 60, 62 and the sensing layer 64, the sensor 42 may also include a temperature probe 66 (see FIGS. 6 and 8), a mass transport limiting layer 74 (see FIG. 9), a biocompatible layer 75 (see FIG. 9), and/or other optional components, as described below. Each of these items enhances the functioning of and/or results from the sensor 42, as discussed below.

The Substrate

The substrate 50 may be formed using a variety of non-conducting materials, including, for example, polymeric or plastic materials and ceramic materials. Suitable materials for a particular sensor 42 may be determined, at least in part, based on the desired use of the sensor 42 and properties of the materials.

In some embodiments, the substrate is flexible. For example, if the sensor 42 is configured for implantation into a patient, then the sensor 42 may be made flexible (although rigid sensors may also be used for implantable sensors) to reduce pain to the patient and damage to the tissue caused by the implantation of and/or the wearing of the sensor 42. A flexible substrate 50 often increases the patient's comfort and allows a wider range of activities. A flexible substrate 50 is also useful for an in vitro sensor 42, particularly for ease of manufacturing. Suitable materials for a flexible substrate 50 include, for example, non-conducting plastic or polymeric materials and other non-conducting, flexible, deformable materials. Examples of useful plastic or polymeric materials include thermoplastics such as polycarbonates, polyesters (e.g., Mylar™ and polyethylene terephthalate (PET)), polyvinyl chloride (PVC), polyurethanes, polyethers, polyamides, polyimides, or copolymers of these thermoplastics, such as PETG (glycol-modified polyethylene terephthalate).

In other embodiments, the sensors 42 are made using a relatively rigid substrate 50 to, for example, provide structural support against bending or breaking. Examples of rigid materials that may be used as the substrate 50 include poorly conducting ceramics, such as aluminum oxide and silicon dioxide. One advantage of an implantable sensor 42 having a rigid substrate is that the sensor 42 may have a sharp point and/or a sharp edge to aid in implantation of a sensor 42 without an additional insertion device. In addition, rigid substrates 50 may also be used in sensors for in vitro analyte monitors.

It will be appreciated that for many sensors 42 and sensor applications, both rigid and flexible sensors will operate adequately. The flexibility of the sensor 42 may also be controlled and varied along a continuum by changing, for example, the composition and/or thickness of the substrate 50.

In addition to considerations regarding flexibility, it is often desirable that implantable sensors 42, as well as in vitro sensors which contact a fluid that is returned to a patient's body, should have a substrate 50 which is non-toxic. Preferably, the substrate 50 is approved by one or more appropriate governmental agencies or private groups for in vivo use.

Figure 17:
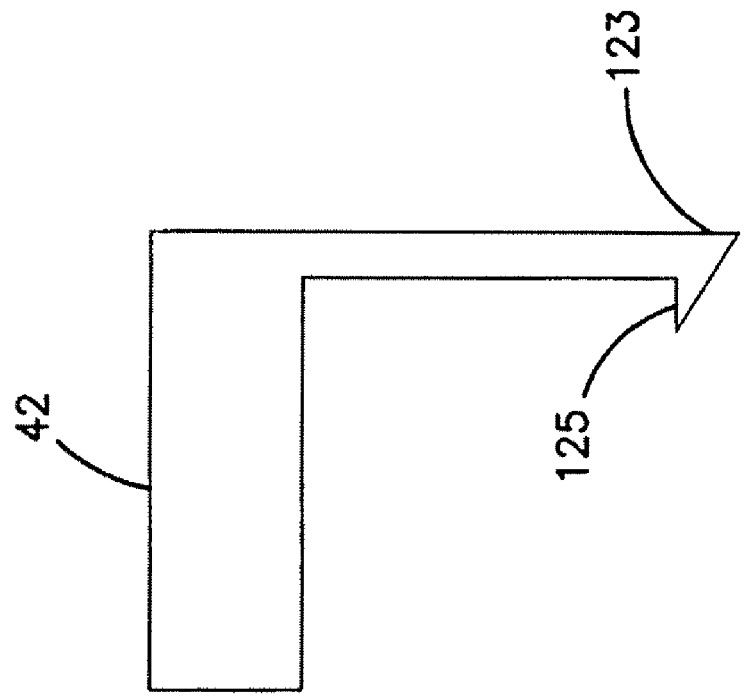
FIG. 17 is a top view of another embodiment of an analyte sensor, according to the invention.

The sensor 42 may include optional features to facilitate insertion of an implantable sensor 42, as shown in FIG. 17. For example, the sensor 42 may be pointed at the tip 123 to ease insertion. In addition, the sensor 42 may include a barb 125 which assists in anchoring the sensor 42 within the tissue of the patient during operation of the sensor 42. However, the barb 125 is typically small enough that little damage is caused to the subcutaneous tissue when the sensor 42 is removed for replacement.

Although the substrate 50 in at least some embodiments has uniform dimensions along the entire length of the sensor 42, in other embodiments, the substrate 50 has a distal end 67 at a first portion 67a of sensor 42 and a proximal end 65 at a second portion 65a of sensor 42. First portion 67a and second portion 65a have different widths 53, 55, respectively, as illustrated in FIG. 2. Width 53 is measured between edge 67' and edge 67" of first portion 67a, and width 55 is measured between edge 65' and edge 65" of second portion 65a. In these embodiments, the first portion 67a having distal end 67 of the substrate 50 may have a relatively narrow width 53. For sensors 42 which are implantable into the subcutaneous tissue or another portion of a patient's body, the narrow width 53 of the first portion 67a having distal end 67 of the substrate 50 may facilitate the implantation of the sensor 42. Often, the narrower the width of the sensor 42, the less pain the patient will feel during implantation of the sensor and afterwards.

For subcutaneously implantable sensors 42 which are designed for continuous or periodic monitoring of the analyte during normal activities of the patient, the first portion 67a having distal end 67 of the sensor 42 which is to be implanted into the patient has a width 53 of 2 mm or less, preferably 1 mm or less, and more preferably 0.5 mm or less. If the sensor 42 does not have regions of different widths, then the sensor 42 will typically have an overall width of, for example, 2 mm, 1.5 mm, 1 mm, 0.5 mm, 0.25 mm, or less. However, wider or narrower sensors may be used. In particular, wider implantable sensors may be used for insertion into veins or arteries or when the movement of the patient is limited, for example, when the patient is confined in bed or in a hospital.

For sensors 42 which are designed for measuring small volume in vitro samples, the narrow width 53 may reduce the volume of sample needed for an accurate reading. The narrow width 53 of the sensor 42 results in all of the electrodes of the sensor 42 being closely congregated, thereby requiring less sample volume to cover all of the electrodes. The width of an in vitro sensor 42 may vary depending, at least in part, on the volume of sample available to the sensor 42 and the dimensions of the sample chamber in which the sensor 42 is disposed.

Returning to FIG. 2, the proximal end 65 of the sensor 42 may have a width 55 larger than the distal end 67 to facilitate the connection between contact pads 49 of the electrodes and contacts on a control unit. The wider the sensor 42 at this point, the larger the contact pads 49 can be made. This may reduce the precision needed to properly connect the sensor 42 to contacts on the control unit (e.g., sensor control unit 44 of FIG. 1). However, the maximum width of the sensor 42 may be constrained so that the sensor 42 remains small for the convenience and comfort of the patient and/or to fit the desired size of the analyte monitor. For example, the proximal end 65 of a subcutaneously implantable sensor 42, such as the sensor 42 illustrated in FIG. 1, may have a width 55 ranging from 0.5 mm to 15 mm, preferably from 1 mm to 10 mm, and more preferably from 3 mm to 7 mm. However, wider or narrower sensors may be used in this and other in vivo and in vitro applications.

The thickness of the substrate 50 may be determined by the mechanical properties of the substrate material (e.g., the strength, modulus, and/or flexibility of the material), the desired use of the sensor 42 including stresses on the substrate 50 arising from that use, as well as the depth of any channels or indentations formed in the substrate 50, as discussed below. Typically, the substrate 50 of a subcutaneously implantable sensor 42 for continuous or periodic monitoring of the level of an analyte while the patient engages in normal activities has a thickness of 50 to 500 µm and preferably 100 to 300 µm. However, thicker and thinner substrates 50 may be used, particularly in other types of in vivo and in vitro sensors 42.

The length of the sensor 42 may have a wide range of values depending on a variety of factors. Factors which influence the length of an implantable sensor 42 may include the depth of implantation into the patient and the ability of the patient to manipulate a small flexible sensor 42 and make connections between the sensor 42 and the sensor control unit 44. A subcutaneously implantable sensor 42 for the analyte monitor illustrated in FIG. 1 may have a length ranging from 0.3 to 5 cm, however, longer or shorter sensors may be used. The length of the narrow portion of the sensor 42 (e.g., the portion which is subcutaneously inserted into the patient), if the sensor 42 has narrow and wide portions, is typically about 0.25 to 2 cm in length. However, longer and shorter portions may be used. All or only a part of this narrow portion may be subcutaneously implanted into the patient.

The lengths of other implantable sensors 42 will vary depending, at least in part, on the portion of the patient into which the sensor 42 is to be implanted or inserted. The length of in vitro sensors may vary over a wide range depending on the particular configuration of the analyte monitoring system and, in particular, the distance between the contacts of the control unit and the sample.

Conductive Traces

At least one conductive trace 52 is formed on the substrate for use in constructing a working electrode 58. In addition, other conductive traces 52 may be formed on the substrate 50 for use as electrodes (e.g., additional working electrodes, as well as counter, counter/reference, and/or reference electrodes) and other components, such as a temperature probe. The conductive traces 52 may extend most of the distance along a length 57 of the sensor 50, as illustrated in FIG. 2, although this is not necessary. The placement of the conductive traces 52 may depend on the particular configuration of the analyte monitoring system (e.g., the placement of control unit contacts and/or the sample chamber in relation to the sensor 42). For implantable sensors, particularly subcutaneously implantable sensors, the conductive traces typically extend close to the tip of the sensor 42 to minimize the amount of the sensor that must be implanted.

The conductive traces 52 may be formed on the substrate 50 by a variety of techniques, including, for example, photolithography, screen printing, or other impact or non-impact printing techniques. The conductive traces 52 may also be formed by carbonizing conductive traces 52 in an organic (e.g., polymeric or plastic) substrate 50 using a laser.

Figure 3A:
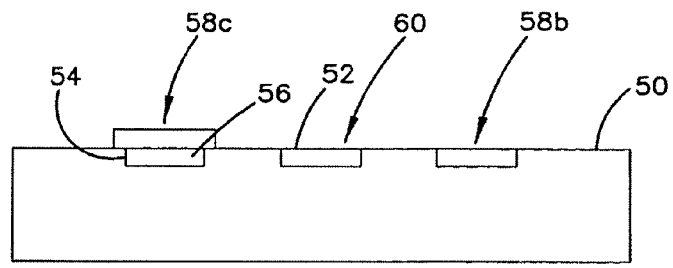
FIG. 3A is a cross-sectional view of the analyte sensor of FIG. 2.

Another method for disposing the conductive traces 52 on the substrate 50 includes the formation of recessed channels 54 in one or more surfaces of the substrate 50 and the subsequent filling of these recessed channels 54 with a conductive material 56, as shown in FIG. 3A. The recessed channels 54 may be formed by indenting, embossing, or otherwise creating a depression in the surface of the substrate 50. The depth of the channels is typically related to the thickness of the substrate 50. In one embodiment, the channels have depths in the range of about 12.5 to 75 µm (0.5 to 3 mils), and preferably about 25 to 50 µm (1 to 2 mils).

The conductive traces are typically formed using a conductive material 56 such as carbon (e.g., graphite), a conductive polymer, a metal or alloy (e.g., gold or gold alloy), or a metallic compound (e.g., ruthenium dioxide or titanium dioxide). The formation of films of carbon, conductive polymer, metal, alloy, or metallic compound are well-known and include, for example, chemical vapor deposition (CVD), physical vapor deposition, sputtering, reactive sputtering, printing, coating, and painting. The conductive material 56 which fills the channels 54 is often formed using a precursor material, such as a conductive ink or paste. In these embodiments, the conductive material 56 is deposited on the substrate 50 using methods such as coating, painting, or applying the material using a spreading instrument, such as a coating blade. Excess conductive material between the channels 54 is then removed by, for example, running a blade along the substrate surface.

In one embodiment, the conductive material 56 is a part of a precursor material, such as a conductive ink, obtainable, for example, from Ercon, Inc. (Wareham, Mass.), Metech, Inc. (Elverson, Pa.), E.I. du Pont de Nemours and Co. (Wilmington, Del.), Emca-Remex Products (Montgomeryville, Pa.), or MCA Services (Melbourn, Great Britain). The conductive ink is typically applied as a semiliquid or paste which contains particles of the carbon, metal, alloy, or metallic compound and a solvent or dispersant. After application of the conductive ink on the substrate 50 (e.g., in the channels 54), the solvent or dispersant evaporates to leave behind a solid mass of conductive material 56.

In addition to the particles of carbon, metal, alloy, or metallic compound, the conductive ink may also contain a binder. The binder may optionally be cured to further bind the conductive material 56 within the channel 54 and/or on the substrate 50. Curing the binder increases the conductivity of the conductive material 56. However, this is typically not necessary as the currents carried by the conductive material 56 within the conductive traces 52 are often relatively low (usually less than 1 µA and often less than 100 nA). Typical binders include, for example, polyurethane resins, cellulose derivatives, elastomers, and highly fluorinated polymers. Examples of elastomers include silicones, polymeric dienes, and acrylonitrile-butadiene-styrene (ABS) resins. One example of a fluorinated polymer binder is Teflon® (DuPont, Wilmington, Del.). These binders are cured using, for example, heat or light, including ultraviolet (UV) light. The appropriate curing method typically depends on the particular binder which is used.

Often, when a liquid or semiliquid precursor of the conductive material 56 (e.g., a conductive ink) is deposited in the channel 54, the precursor fills the channel 54. However, when the solvent or dispersant evaporates, the conductive material 56 which remains may lose volume such that the conductive material 56 may or may not continue to fill the channel 54. Preferred conductive materials 56 do not pull away from the substrate 50 as they lose volume, but rather decrease in height within the channel 54. These conductive materials 56 typically adhere well to the substrate 50 and therefore do not pull away from the substrate 50 during evaporation of the solvent or dispersant. Other suitable conductive materials 56 either adhere to at least a portion of the substrate 50 and/or contain another additive, such as a binder, which adheres the conductive material 56 to the substrate 50. Preferably, the conductive material 56 in the channels 54 is non-leachable, and more preferably immobilized on the substrate 50. In some embodiments, the conductive material 56 may be formed by multiple applications of a liquid or semiliquid precursor interspersed with removal of the solvent or dispersant.

In another embodiment, the channels 54 are formed using a laser. The laser carbonizes the polymer or plastic material. The carbon formed in this process is used as the conductive material 56. Additional conductive material 56, such as a conductive carbon ink, may be used to supplement the carbon formed by the laser.

In a further embodiment, the conductive traces 52 are formed by pad printing techniques. For example, a film of conductive material is formed either as a continuous film or as a coating layer deposited on a carrier film. This film of conductive material is brought between a print head and the substrate 50. A pattern on the surface of the substrate 50 is made using the print head according to a desired pattern of conductive traces 52. The conductive material is transferred by pressure and/or heat from the film of conductive material to the substrate 50. This technique often produces channels (e.g., depressions caused by the print head) in the substrate 50. Alternatively, the conductive material is deposited on the surface of the substrate 50 without forming substantial depressions.

In other embodiments, the conductive traces 52 are formed by non-impact printing techniques. Such techniques include electrophotography and magnetography. In these processes, an image of the conductive traces 52 is electrically or magnetically formed on a drum. A laser or LED may be used to electrically form an image. A magnetic recording head may be used to magnetically form an image. A toner material (e.g., a conductive material, such as a conductive ink) is then attracted to portions of the drum according to the image. The toner material is then applied to the substrate by contact between the drum and the substrate. For example, the substrate may be rolled over the drum. The toner material may then be dried and/or a binder in the toner material may be cured to adhere the toner material to the substrate.

Another non-impact printing technique includes ejecting droplets of conductive material onto the substrate in a desired pattern. Examples of this technique include ink jet printing and piezo jet printing. An image is sent to the printer which then ejects the conductive material (e.g., a conductive ink) according to the pattern. The printer may provide a continuous stream of conductive material or the printer may eject the conductive material in discrete amounts at the desired points.

Yet another non-impact printing embodiment of forming the conductive traces includes an ionographic process. In this process, a curable, liquid precursor, such as a photopolymerizable acrylic resin (e.g., Solimer 7501 from Cubital, Bad Kreuznach, Germany) is deposited over a surface of a substrate 50. A photomask having a positive or negative image of the conductive traces 52 is then used to cure the liquid precursor. Light (e.g., visible or ultraviolet light) is directed through the photomask to cure the liquid precursor and form a solid layer over the substrate according to the image on the photomask. Uncured liquid precursor is removed leaving behind channels 54 in the solid layer. These channels 54 can then be filled with conductive material 56 to form conductive traces 52.

Conductive traces 52 (and channels 54, if used) can be formed with relatively narrow widths, for example, in the range of 25 to 250 µm, and including widths of, for example, 250 µm, 150 µm, 100 µm, 75 µm, 50 µm, 25 µm or less by the methods described above. In embodiments with two or more conductive traces 52 on the same side of the substrate 50, the conductive traces 52 are separated by distances sufficient to prevent conduction between the conductive traces 52. The edge-to-edge distance between the conductive traces is preferably in the range of 25 to 250 µm and may be, for example, 150 µm, 100 µm, 75 µm, 50 µm, or less. The density of the conductive traces 52 on the substrate 50 is preferably in the range of about 150 to 700 µm/trace and may be as small as 667 µm/trace or less, 333 µm/trace or less, or even 167 µm/trace or less.

The working electrode 58 and the counter electrode 60 (if a separate reference electrode is used) are often made using a conductive material 56, such as carbon. Suitable carbon conductive inks are available from Ercon, Inc. (Wareham, Mass.), Metech, Inc. (Elverson, Pa.), E.I. du Pont de Nemours and Co. (Wilmington, Del.), Emca-Remex Products (Montgomeryville, Pa.), or MCA Services (Melbourn, Great Britain). Typically, the working surface 51 of the working electrode 58 is at least a portion of the conductive trace 52 that is in contact with the analyte-containing fluid (e.g., implanted in the patient or in the sample chamber of an in vitro analyte monitor).

The reference electrode 62 and/or counter/reference electrode are typically formed using conductive material 56 that is a suitable reference material, for example silver/silver chloride or a non-leachable redox couple bound to a conductive material, for example, a carbon-bound redox couple. Suitable silver/silver chloride conductive inks are available from Ercon, Inc. (Wareham, Mass.), Metech, Inc. (Elverson, Pa.), E.I. du Pont de Nemours and Co. (Wilmington, Del.), Emca-Remex Products (Montgomeryville, Pa.), or MCA Services (Melbourn, Great Britain). Silver/silver chloride electrodes illustrate a type of reference electrode that involves the reaction of a metal electrode with a constituent of the sample or body fluid, in this case, $Cl^-$.

Suitable redox couples for binding to the conductive material of the reference electrode include, for example, redox polymers (e.g., polymers having multiple redox centers.) It is preferred that the reference electrode surface be non-corroding so that an erroneous potential is not measured. Preferred conductive materials include less corrosive metals, such as gold and palladium. Most preferred are non-corrosive materials including non-metallic conductors, such as carbon and conducting polymers. A redox polymer can be adsorbed on or covalently bound to the conductive material of the reference electrode, such as a carbon surface of a conductive trace 52. Non-polymeric redox couples can be similarly bound to carbon or gold surfaces.

A variety of methods may be used to immobilize a redox polymer on an electrode surface. One method is adsorptive immobilization. This method is particularly useful for redox polymers with relatively high molecular weights. The molecular weight of a polymer may be increased, for example, by cross-linking.

Another method for immobilizing the redox polymer includes the functionalization of the electrode surface and then the chemical bonding, often covalently, of the redox polymer to the functional groups on the electrode surface. One example of this type of immobilization begins with a poly(4-vinylpyridine). The polymer's pyridine rings are, in part, complexed with a reducible/oxidizable species, such as $[Os(bpy)_2Cl]^{+/2+}$ where bpy is 2,2'-bipyridine. Part of the pyridine rings are quaternized by reaction with 2-bromoethylamine. The polymer is then crosslinked, for example, using a diepoxide, such as polyethylene glycol diglycidyl ether.

Carbon surfaces can be modified for attachment of a redox species or polymer, for example, by electroreduction of a diazonium salt. As an illustration, reduction of a diazonium salt formed upon diazotization of p-aminobenzoic acid modifies a carbon surface with phenylcarboxylic acid functional groups. These functional groups can then be activated by a carbodiimide, such as 1-ethyl-3-(3-dimethylaminopropyl)-carbodiimide hydrochloride. The activated functional groups are then bound with a amine-functionalized redox couple, such as the quaternized osmium-containing redox polymer described above or 2-aminoethylferrocene, to form the redox couple.

Similarly, gold can be functionalized by an amine, such as cystamine. A redox couple such as $[Os(bpy)_2(pyridine-4-carboxylate)Cl]^{0/+}$ is activated by 1-ethyl-3-(3-dimethylaminopropyl)-carbodiimide hydrochloride to form a reactive O-acylisourea which reacts with the gold-bound amine to form an amide.

In one embodiment, in addition to using the conductive traces 52 as electrodes or probe leads, two or more of the conductive traces 52 on the substrate 50 are used to give the patient a mild electrical shock when, for example, the analyte level exceeds a threshold level. This shock may act as a warning or alarm to the patient to initiate some action to restore the appropriate level of the analyte.

The mild electrical shock is produced by applying a potential between any two conductive traces 52 that are not otherwise connected by a conductive path. For example, two of the electrodes 58, 60, 62 or one electrode 58, 60, 62 and the temperature probe 66 may be used to provide the mild shock. Preferably, the working electrode 58 and the reference electrode 62 are not used for this purpose as this may cause some damage to the chemical components on or proximate to the particular electrode (e.g., the sensing layer on the working electrode or the redox couple on the reference electrode).

The current used to produce the mild shock is typically 0.1 to 1 mA. Higher or lower currents may be used, although care should be taken to avoid harm to the patient. The potential between the conductive traces is typically 1 to 10 volts. However, higher or lower voltages may be used depending, for example, on the resistance of the conductive traces 52, the distance between the conductive traces 52 and the desired amount of current. When the mild shock is delivered, potentials at the working electrode 58 and across the temperature probe 66 may be removed to prevent harm to those components caused by unwanted conduction between the working electrode 58 (and/or temperature probe 66, if used) and the conductive traces 52 which provide the mild shock.

Contact Pads

Typically, each of the conductive traces 52 includes a contact pad 49. The contact pad 49 may simply be a portion of the conductive trace 52 that is indistinguishable from the rest of the trace 52 except that the contact pad 49 is brought into contact with the conductive contacts of a control unit (e.g., the sensor control unit 44 of FIG. 1). More commonly, however, the contact pad 49 is a region of the conductive trace 52 that has a larger width than other regions of the trace 52 to facilitate a connection with the contacts on the control unit. By making the contact pads 49 relatively large as compared with the width of the conductive traces 52, the need for precise registration between the contact pads 49 and the contacts on the control unit is less critical than with small contact pads.

The contact pads 49 are typically made using the same material as the conductive material 56 of the conductive traces 52. However, this is not necessary. Although metal, alloys, and metallic compounds may be used to form the contact pads 49, in some embodiments, it is desirable to make the contact pads 49 from a carbon or other non-metallic material, such as a conducting polymer. In contrast to metal or alloy contact pads, carbon and other non-metallic contact pads are not easily corroded if the contact pads 49 are in a wet, moist, or humid environment. Metals and alloys may corrode under these conditions, particularly if the contact pads 49 and contacts of the control unit are made using different metals or alloys. However, carbon and non-metallic contact pads 49 do not significantly corrode, even if the contacts of the control device are metal or alloy.

One embodiment of the invention includes a sensor 42 having contact pads 49 and a control unit 44 having conductive contacts (not shown). During operation of the sensor 42, the contact pads 49 and conductive contacts are in contact with each other. In this embodiment, either the contact pads 49 or the conductive contacts are made using a non-corroding, conductive material. Such materials include, for example, carbon and conducting polymers. Preferred non-corroding materials include graphite and vitreous carbon. The opposing contact pad or conductive contact is made using carbon, a conducting polymer, a metal, such as gold, palladium, or platinum group metal, or a metallic compound, such as ruthenium dioxide. This configuration of contact pads and conductive contacts typically reduces corrosion. Preferably, when the sensor is placed in a 3 mM, and more preferably, in a 100 mM, NaCl solution, the signal arising due to the corrosion of the contact pads and/or conductive contacts is less than 3% of the signal generated by the sensor when exposed to concentration of analyte in the normal physiological range. For at least some subcutaneous glucose sensors, the current generated by analyte in a normal physiological range ranges from 3 to 500 nA.

Figure 10:
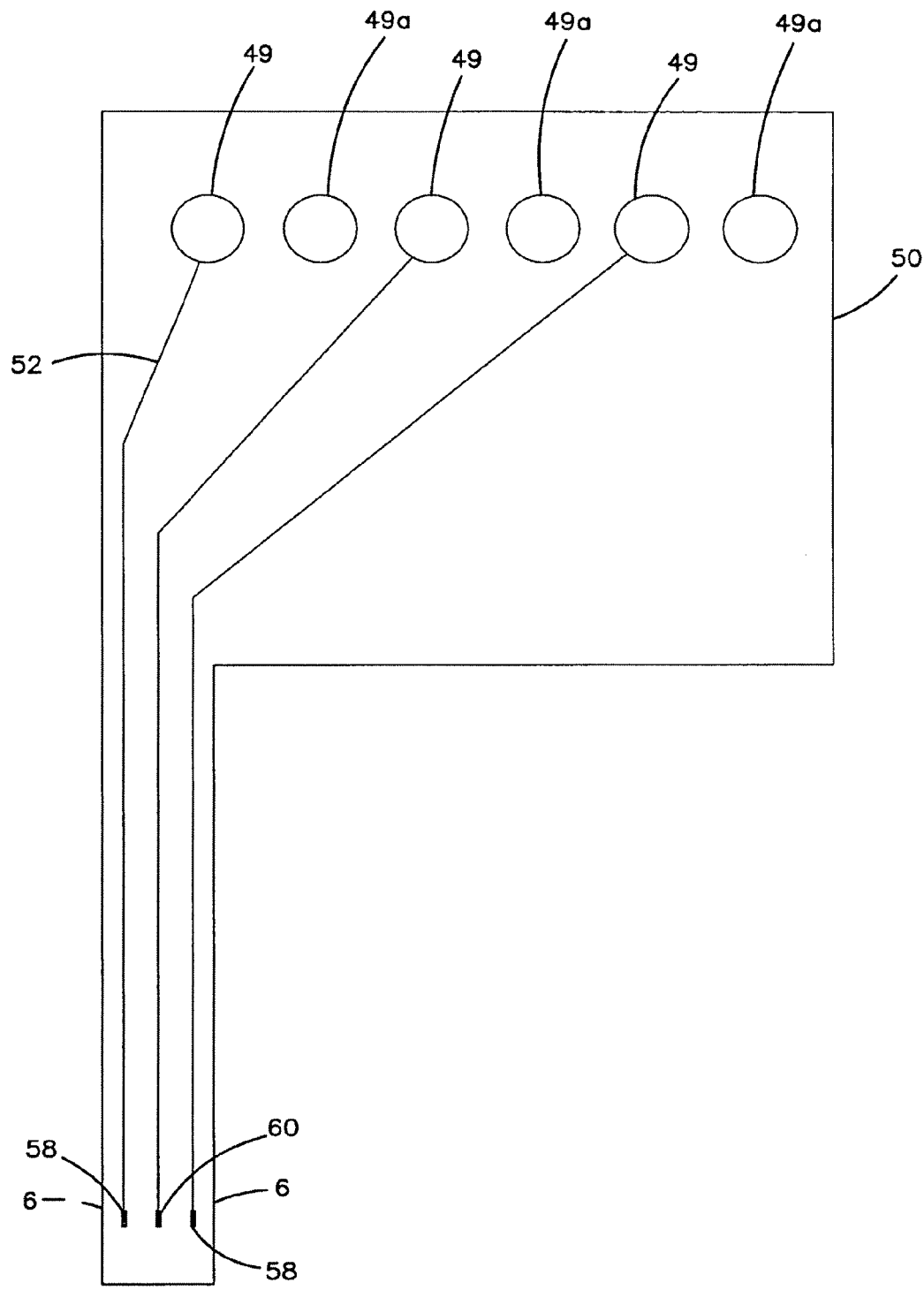
FIG. 10 is a top view of the analyte sensor of FIG. 6.
Figure 11:
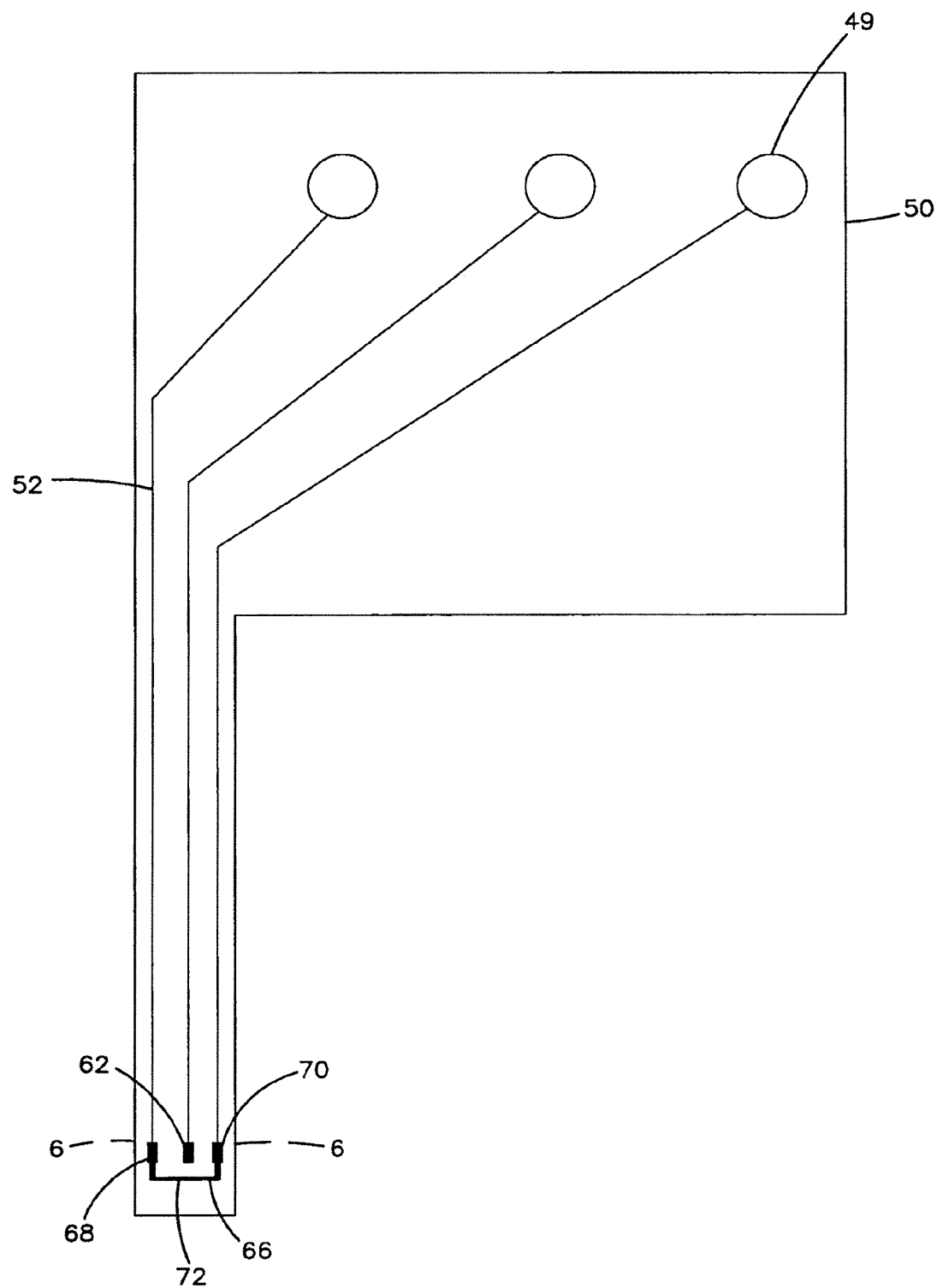
FIG. 11 is a bottom view of the analyte sensor of FIG. 6.

Each of the electrodes 58, 60, 62, as well as the two probe leads 68, 70 of the temperature probe 66 (described below), are connected to contact pads 49 as shown in FIGS. 10 and 11. In one embodiment (not shown), the contact pads 49 are on the same side of the substrate 50 as the respective electrodes or temperature probe leads to which the contact pads 49 are attached.

In other embodiments, the conductive traces 52 on at least one side are connected through vias in the substrate to contact pads 49a on the opposite surface of the substrate 50, as shown in FIGS. 10 and 11. An advantage of this configuration is that contact between the contacts on the control unit and each of the electrodes 58, 60, 62 and the probe leads 68,70 of the temperature probe 66 can be made from a single side of the substrate 50.

In yet other embodiments (not shown), vias through the substrate are used to provide contact pads on both sides of the substrate 50 for each conductive trace 52. The vias connecting the conductive traces 52 with the contact pads 49a can be formed by making holes through the substrate 50 at the appropriate points and then filling the holes with conductive material 56.

Exemplary Electrode Configurations

Figure 3B:
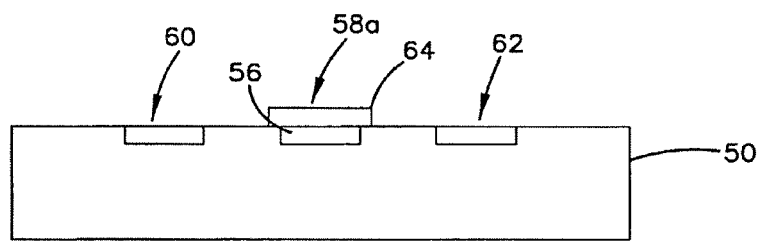
FIG. 3B is a cross-sectional view of another embodiment of an analyte sensor, according to the invention.

A number of exemplary electrode configurations are described below, however, it will be understood that other configurations may also be used. In one embodiment, illustrated in FIG. 3A, the sensor 42 includes two working electrodes 58a, 58b and one counter electrode 60, which also functions as a reference electrode. In another embodiment, the sensor includes one working electrode 58a, one counter electrode 60, and one reference electrode 62, as shown in FIG. 3B. Each of these embodiments is illustrated with all of the electrodes formed on the same side of the substrate 50.

Alternatively, one or more of the electrodes may be formed on an opposing side of the substrate 50. This may be convenient if the electrodes are formed using two different types of conductive material 56 (e.g., carbon and silver/silver chloride). Then, at least in some embodiments, only one type of conductive material 56 needs to be applied to each side of the substrate 50, thereby reducing the number of steps in the manufacturing process and/or easing the registration constraints in the process. For example, if the working electrode 58 is formed using a carbon-based conductive material 56 and the reference or counter/reference electrode is formed using a silver/silver chloride conductive material 56, then the working electrode and reference or counter/reference electrode may be formed on opposing sides of the substrate 50 for ease of manufacture.

Figure 6:
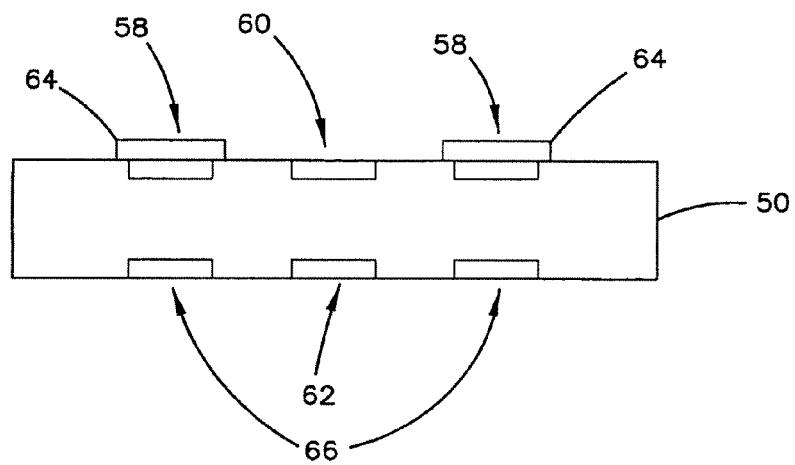
FIG. 6 is a cross-sectional view of a fifth embodiment of an analyte sensor, according to the invention.
Figures 7, 8:
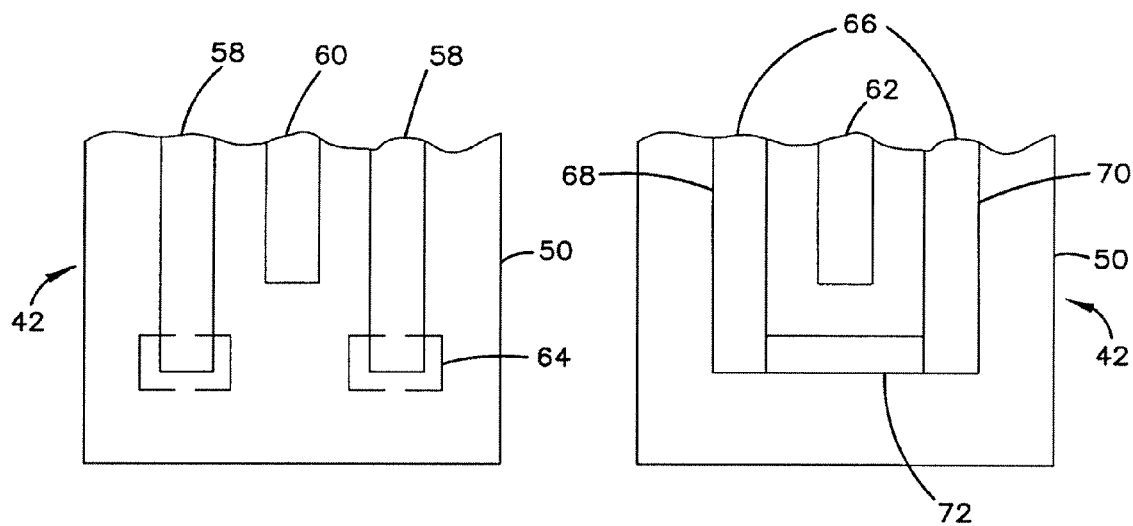
FIG. 7 is an expanded top view of a tip-portion of the analyte sensor of FIG. 6.
FIG. 8 is an expanded bottom view of a tip-portion of the analyte sensor of FIG. 6.

In another embodiment, two working electrodes 58 and one counter electrode 60 are formed on one side of the substrate 50 and one reference electrode 62 and a temperature probe 66 are formed on an opposing side of the substrate 50, as illustrated in FIG. 6. The opposing sides of the tip of this embodiment of the sensor 42 are illustrated in FIGS. 7 and 8.

Sensing Layer

Some analytes, such as oxygen, can be directly electrooxidized or electroreduced on the working electrode 58. Other analytes, such as glucose and lactate, require the presence of at least one electron transfer agent and/or at least one catalyst to facilitate the electrooxidation or electroreduction of the analyte. Catalysts may also be used for those analyte, such as oxygen, that can be directly electrooxidized or electroreduced on the working electrode 58. For these analytes, each working electrode 58 has a sensing layer 64 formed proximate to or on a working surface of the working electrode 58. Typically, the sensing layer 64 is formed near or on only a small portion of the working electrode 58, often near a tip of the sensor 42. This limits the amount of material needed to form the sensor 42 and places the sensing layer 64 in the best position for contact with the analyte-containing fluid (e.g., a body fluid, sample fluid, or carrier fluid).

The sensing layer 64 includes one or more components designed to facilitate the electrolysis of the analyte. The sensing layer 64 may include, for example, a catalyst to catalyze a reaction of the analyte and produce a response at the working electrode 58, an electron transfer agent to indirectly or directly transfer electrons between the analyte and the working electrode 58, or both.

The sensing layer 64 may be formed as a solid composition of the desired components (e.g., an electron transfer agent and/or a catalyst). These components are preferably non-leachable from the sensor 42 and more preferably are immobilized on the sensor 42. For example, the components may be immobilized on a working electrode 58. Alternatively, the components of the sensing layer 64 may be immobilized within or between one or more membranes or films disposed over the working electrode 58 or the components may be immobilized in a polymeric or sol-gel matrix. Examples of immobilized sensing layers are described in U.S. Pat. Nos. 5,262,035, 5,264,104, 5,264,105, 5,320,725, 5,593,852, and 5,665,222, and PCT Patent Application Publication No. WO 98/35053, incorporated herein by reference.

In some embodiments, one or more of the components of the sensing layer 64 may be solvated, dispersed, or suspended in a fluid within the sensing layer 64, instead of forming a solid composition. The fluid may be provided with the sensor 42 or may be absorbed by the sensor 42 from the analyte-containing fluid. Preferably, the components which are solvated, dispersed, or suspended in this type of sensing layer 64 are non-leachable from the sensing layer. Non-leachability may be accomplished, for example, by providing barriers (e.g., the electrode, substrate, membranes, and/or films) around the sensing layer which prevent the leaching of the components of the sensing layer 64. One example of such a barrier is a microporous membrane or film which allows diffusion of the analyte into the sensing layer 64 to make contact with the components of the sensing layer 64, but reduces or eliminates the diffusion of the sensing layer components (e.g., a electron transfer agent and/or a catalyst) out of the sensing layer 64.

A variety of different sensing layer configurations can be used. In one embodiment, the sensing layer 64 is deposited on the conductive material 56 of a working electrode 58a, as illustrated in FIGS. 3A and 3B. The sensing layer 64 may extend beyond the conductive material 56 of the working electrode 58a. In some cases, the sensing layer 64 may also extend over the counter electrode 60 or reference electrode 62 without degrading the performance of the glucose sensor. For those sensors 42 which utilize channels 54 within which the conductive material 56 is deposited, a portion of the sensing layer 64 may be formed within the channel 54 if the conductive material 56 does not fill the channel 54.

A sensing layer 64 in direct contact with the working electrode 58a may contain an electron transfer agent to transfer electrons directly or indirectly between the analyte and the working electrode, as well as a catalyst to facilitate a reaction of the analyte. For example, a glucose, lactate, or oxygen electrode may be formed having a sensing layer which contains a catalyst, such as glucose oxidase, lactate oxidase, or laccase, respectively, and an electron transfer agent that facilitates the electrooxidation of the glucose, lactate, or oxygen, respectively.

Figure 4A:
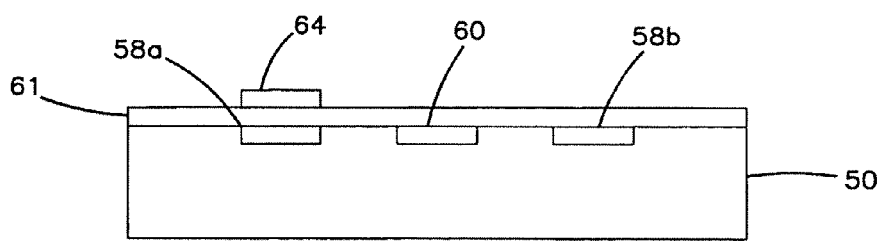
FIG. 4A is a cross-sectional view of yet another embodiment of an analyte sensor, according to the invention.

In another embodiment, the sensing layer 64 is not deposited directly on the working electrode 58a. Instead, the sensing layer 64 is spaced apart from the working electrode 58a, as illustrated in FIG. 4A, and separated from the working electrode 58a by a separation layer 61. The separation layer 61 typically includes one or more membranes or films. In addition to separating the working electrode 58a from the sensing layer 64, the separation layer 61 may also act as a mass transport limiting layer or an interferent eliminating layer, as described below.

Typically, a sensing layer 64, which is not in direct contact with the working electrode 58a, includes a catalyst that facilitates a reaction of the analyte. However, this sensing layer 64 typically does not include an electron transfer agent that transfers electrons directly from the working electrode 58a to the analyte, as the sensing layer 64 is spaced apart from the working electrode 58a. One example of this type of sensor is a glucose or lactate sensor which includes an enzyme (e.g., glucose oxidase or lactate oxidase, respectively) in the sensing layer 64. The glucose or lactate reacts with a second compound (e.g., oxygen) in the presence of the enzyme. The second compound is then electrooxidized or electroreduced at the electrode. Changes in the signal at the electrode indicate changes in the level of the second compound in the fluid and are proportional to changes in glucose or lactate level and, thus, correlate to the analyte level.

Figure 4B:
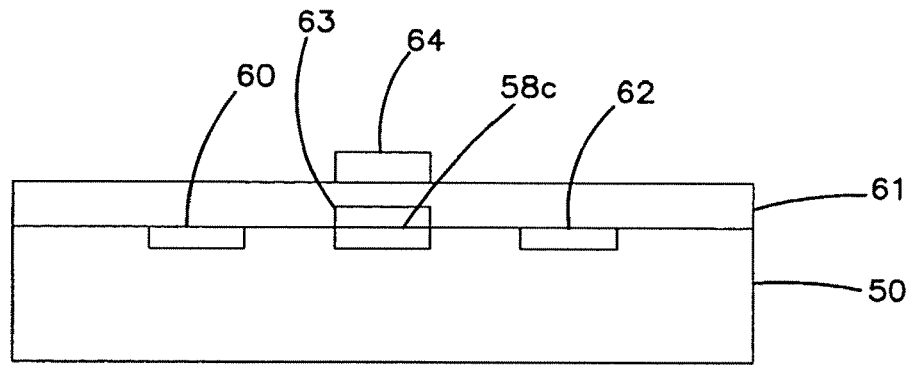
FIG. 4B is a cross-sectional view of a fourth embodiment of an analyte sensor, according to the invention.
Figure 5:
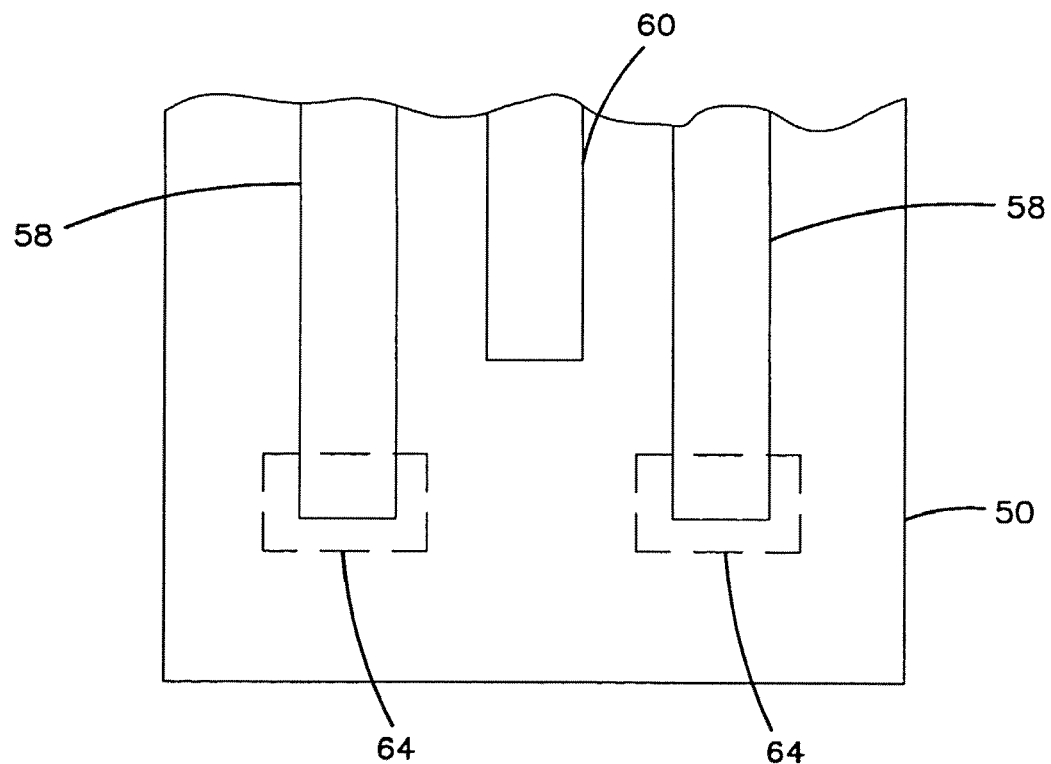
FIG. 5 is an expanded top view of a tip portion of the analyte sensor of FIG. 2.

In another embodiment, two sensing layers 63, 64 are used, as shown in FIG. 4B. Each of the two sensing layers 63, 64 may be independently formed on the working electrode 58a or in proximity to the working electrode 58a. One sensing layer 64 is typically, although not necessarily, spaced apart from the working electrode 58a. For example, this sensing layer 64 may include a catalyst which catalyzes a reaction of the analyte to form a product compound. The product compound is then electrolyzed in the second sensing layer 63 which may include an electron transfer agent to transfer electrons between the working electrode 58a and the product compound and/or a second catalyst to catalyze a reaction of the product compound to generate a signal at the working electrode 58a.

For example, a glucose or lactate sensor may include a first sensing layer 64 which is spaced apart from the working electrode and contains an enzyme, for example, glucose oxidase or lactate oxidase. The reaction of glucose or lactate in the presence of the appropriate enzyme forms hydrogen peroxide. A second sensing layer 63 is provided directly on the working electrode 58a and contains a peroxidase enzyme and an electron transfer agent to generate a signal at the electrode in response to the hydrogen peroxide. The level of hydrogen peroxide indicated by the sensor then correlates to the level of glucose or lactate. Another sensor which operates similarly can be made using a single sensing layer with both the glucose or lactate oxidase and the peroxidase being deposited in the single sensing layer. Examples of such sensors are described in U.S. Pat. Nos. 5,593,852, 5,665,222 and PCT Patent Application Publication No. WO 98/35053, incorporated herein by reference.

In some embodiments, one or more of the working electrodes 58b do not have a corresponding sensing layer 64, as shown in FIGS. 3A and 4A, or have a sensing layer (not shown) which does not contain one or more components (e.g., an electron transfer agent or catalyst) needed to electrolyze the analyte. The signal generated at this working electrode 58b typically arises from interferents and other sources, such as ions, in the fluid, and not in response to the analyte (because the analyte is not electrooxidized or electroreduced). Thus, the signal at this working electrode 58b corresponds to a background signal. The background signal can be removed from the analyte signal obtained from other working electrodes 58a that are associated with fully-functional sensing layers 64 by, for example, subtracting the signal at working electrode 58b from the signal at working electrode 58a.

Sensors having multiple working electrodes 58a may also be used to obtain more precise results by averaging the signals or measurements generated at these working electrodes 58a. In addition, multiple readings at a single working electrode 58a or at multiple working electrodes may be averaged to obtain more precise data.

Electron Transfer Agent

In many embodiments, the sensing layer 64 contains one or more electron transfer agents in contact with the conductive material 56 of the working electrode 58, as shown in FIGS. 3A and 3B. In some embodiments, it is acceptable for the electron transfer agent to diffuse or leach away from the working electrode, particularly for in vitro sensors 42 that are used only once. Other in vitro sensors may utilize a carrier fluid which contains the electron transfer agent. The analyte is transferred to the carrier fluid from the original sample fluid by, for example, osmotic flow through a microporous membrane or the like.

In yet other embodiments of the invention, there is little or no leaching of the electron transfer agent away from the working electrode 58 during the period in which the sensor 42 is implanted in the patient or measuring an in vitro analyte-containing sample. A diffusing or leachable (i.e., releasable) electron transfer agent often diffuses into the analyte-containing fluid, thereby reducing the effectiveness of the electrode by reducing the sensitivity of the sensor over time. In addition, a diffusing or leaching electron transfer agent in an implantable sensor 42 may also cause damage to the patient. In these embodiments, preferably, at least 90%, more preferably, at least 95%, and, most preferably, at least 99%, of the electron transfer agent remains disposed on the sensor after immersion in the analyte-containing fluid for 24 hours, and, more preferably, for 72 hours. In particular, for an implantable sensor, preferably, at least 90%, more preferably, at least 95%, and most preferably, at least 99%, of the electron transfer agent remains disposed on the sensor after immersion in the body fluid at 37° C. for 24 hours, and, more preferably, for 72 hours.

In some embodiments of the invention, to prevent leaching, the electron transfer agents are bound or otherwise immobilized on the working electrode 58 or between or within one or more membranes or films disposed over the working electrode 58. The electron transfer agent may be immobilized on the working electrode 58 using, for example, a polymeric or sol-gel immobilization technique. Alternatively, the electron transfer agent may be chemically (e.g., ionically, covalently, or coordinatively) bound to the working electrode 58, either directly or indirectly through another molecule, such as a polymer, that is in turn bound to the working electrode 58.

Application of the sensing layer 64 on a working electrode 58a is one method for creating a working surface for the working electrode 58a, as shown in FIGS. 3A and 3B. The electron transfer agent mediates the transfer of electrons to electrooxidize or electroreduce an analyte and thereby permits a current flow between the working electrode 58 and the counter electrode 60 via the analyte. The mediation of the electron transfer agent facilitates the electrochemical analysis of analytes which are not suited for direct electrochemical reaction on an electrode.

In general, the preferred electron transfer agents are electroreducible and electrooxidizable ions or molecules having redox potentials that are a few hundred millivolts above or below the redox potential of the standard calomel electrode (SCE). Preferably, the electron transfer agents are not more reducing than about −150 mV and not more oxidizing than about +400 mV versus SCE.

The electron transfer agent may be organic, organometallic, or inorganic. Examples of organic redox species are quinones and species that in their oxidized state have quinoid structures, such as Nile blue and indophenol. Some quinones and partially oxidized quinhydrones react with functional groups of proteins such as the thiol groups of cysteine, the amine groups of lysine and arginine, and the phenolic groups of tyrosine which may render those redox species unsuitable for some of the sensors of the present invention because of the presence of the interfering proteins in an analyte-containing fluid. Usually substituted quinones and molecules with quinoid structure are less reactive with proteins and are preferred. A preferred tetrasubstituted quinone usually has carbon atoms in positions 1, 2, 3, and 4.

In general, electron transfer agents suitable for use in the invention have structures or charges which prevent or substantially reduce the diffusional loss of the electron transfer agent during the period of time that the sample is being analyzed. The preferred electron transfer agents include a redox species bound to a polymer which can in turn be immobilized on the working electrode. The bond between the redox species and the polymer may be covalent, coordinative, or ionic. Useful electron transfer agents and methods for producing them are described in U.S. Pat. Nos. 5,264,104; 5,356,786; 5,262,035; and 5,320,725, incorporated herein by reference. Although any organic or organometallic redox species can be bound to a polymer and used as an electron transfer agent, the preferred redox species is a transition metal compound or complex. The preferred transition metal compounds or complexes include osmium, ruthenium, iron, and cobalt compounds or complexes. The most preferred are osmium compounds and complexes. It will be recognized that many of the redox species described below may also be used, typically without a polymeric component, as electron transfer agents in a carrier fluid or in a sensing layer of a sensor where leaching of the electron transfer agent is acceptable.

One type of non-releasable polymeric electron transfer agent contains a redox species covalently bound in a polymeric composition. An example of this type of mediator is poly(vinylferrocene).

Another type of non-releasable electron transfer agent contains an ionically-bound redox species. Typically, this type of mediator includes a charged polymer coupled to an oppositely charged redox species. Examples of this type of mediator include a negatively charged polymer such as Nafion® (DuPont) coupled to a positively charged redox species such as an osmium or ruthenium polypyridyl cation. Another example of an ionically-bound mediator is a positively charged polymer such as quaternized poly(4-vinyl pyridine) or poly(1-vinyl imidazole) coupled to a negatively charged redox species such as ferricyanide or ferrocyanide. The preferred ionically-bound redox species is a highly charged redox species bound within an oppositely charged redox polymer.

In another embodiment of the invention, suitable non-releasable electron transfer agents include a redox species coordinatively bound to a polymer. For example, the mediator may be formed by coordination of an osmium or cobalt 2,2'-bipyridyl complex to poly(1-vinyl imidazole) or poly(4-vinyl pyridine).

The preferred electron transfer agents are osmium transition metal complexes with one or more ligands, each ligand having a nitrogen-containing heterocycle such as 2,2'-bipyridine, 1,10-phenanthroline, or derivatives thereof. Furthermore, the preferred electron transfer agents also have one or more ligands covalently bound in a polymer, each ligand having at least one nitrogen-containing heterocycle, such as pyridine, imidazole, or derivatives thereof. These preferred electron transfer agents exchange electrons rapidly between each other and the working electrodes 58 so that the complex can be rapidly oxidized and reduced.

One example of a particularly useful electron transfer agent includes (a) a polymer or copolymer having pyridine or imidazole functional groups and (b) osmium cations complexed with two ligands, each ligand containing 2,2'-bipyridine, 1,10-phenanthroline, or derivatives thereof, the two ligands not necessarily being the same. Preferred derivatives of 2,2'-bipyridine for complexation with the osmium cation are 4,4'-dimethyl-2,2'-bipyridine and mono-, di-, and polyalkoxy-2,2'-bipyridines, such as 4,4'-dimethoxy-2,2'-bipyridine. Preferred derivatives of 1,10-phenanthroline for complexation with the osmium cation are 4,7-dimethyl-1,10-phenanthroline and mono-, di-, and polyalkoxy-1,10-phenanthrolines, such as 4,7-dimethoxy-1,10-phenanthroline. Preferred polymers for complexation with the osmium cation include polymers and copolymers of poly(1-vinyl imidazole) (referred to as "PVI") and poly(4-vinyl pyridine) (referred to as "PVP"). Suitable copolymer substituents of poly(1-vinyl imidazole) include acrylonitrile, acrylamide, and substituted or quaternized N-vinyl imidazole. Most preferred are electron transfer agents with osmium complexed to a polymer or copolymer of poly(1-vinyl imidazole).

The preferred electron transfer agents have a redox potential ranging from −100 mV to about +150 mV versus the standard calomel electrode (SCE). Preferably, the potential of the electron transfer agent ranges from −100 mV to +150 mV and more preferably, the potential ranges from −50 mV to +50 mV. The most preferred electron transfer agents have osmium redox centers and a redox potential ranging from +50 mV to −150 mV versus SCE.

Catalyst

The sensing layer 64 may also include a catalyst which is capable of catalyzing a reaction of the analyte. The catalyst may also, in some embodiments, act as an electron transfer agent. One example of a suitable catalyst is an enzyme which catalyzes a reaction of the analyte. For example, a catalyst, such as a glucose oxidase, glucose dehydrogenase (e.g., pyrroloquinoline quinone glucose dehydrogenase (PQQ)), or oligosaccharide dehydrogenase, may be used when the analyte is glucose. A lactate oxidase or lactate dehydrogenase may be used when the analyte is lactate. Laccase may be used when the analyte is oxygen or when oxygen is generated or consumed in response to a reaction of the analyte.

Preferably, the catalyst is non-leachably disposed on the sensor, whether the catalyst is part of a solid sensing layer in the sensor or solvated in a fluid within the sensing layer. More preferably, the catalyst is immobilized within the sensor (e.g., on the electrode and/or within or between a membrane or film) to prevent unwanted leaching of the catalyst away from the working electrode 58 and into the patient. This may be accomplished, for example, by attaching the catalyst to a polymer, cross linking the catalyst with another electron transfer agent (which, as described above, can be polymeric), and/or providing one or more barrier membranes or films with pore sizes smaller than the catalyst.

As described above, a second catalyst may also be used. This second catalyst is often used to catalyze a reaction of a product compound resulting from the catalyzed reaction of the analyte. The second catalyst typically operates with an electron transfer agent to electrolyze the product compound to generate a signal at the working electrode. Alternatively, the second catalyst may be provided in an interferent-eliminating layer to catalyze reactions that remove interferents, as described below.

One embodiment of the invention is an electrochemical sensor in which the catalyst is mixed or dispersed in the conductive material 56 which forms the conductive trace 52 of a working electrode 58. This may be accomplished, for example, by mixing a catalyst, such as an enzyme, in a carbon ink and applying the mixture into a channel 54 on the surface of the substrate 50. Preferably, the catalyst is immobilized in the channel 53 so that it cannot leach away from the working electrode 58. This may be accomplished, for example, by curing a binder in the carbon ink using a curing technique appropriate to the binder. Curing techniques include, for example, evaporation of a solvent or dispersant, exposure to ultraviolet light, or exposure to heat. Typically, the mixture is applied under conditions that do not substantially degrade the catalyst. For example, the catalyst may be an enzyme that is heat-sensitive. The enzyme and conductive material mixture should be applied and cured, preferably, without sustained periods of heating. The mixture may be cured using evaporation or UV curing techniques or by the exposure to heat that is sufficiently short that the catalyst is not substantially degraded.

Another consideration for in vivo analyte sensors is the thermostability of the catalyst. Many enzymes have only limited stability at biological temperatures. Thus, it may be necessary to use large amounts of the catalyst and/or use a catalyst that is thermostable at the necessary temperature (e.g., 37° C. or higher for normal body temperature). A thermostable catalyst may be defined as a catalyst which loses less than 5% of its activity when held at 37° C. for at least one hour, preferably, at least one day, and more preferably at least three days. One example of a thermostable catalyst is soybean peroxidase. This particular thermostable catalyst may be used in a glucose or lactate sensor when combined either in the same or separate sensing layers with glucose or lactate oxidase or dehydrogenase. A further description of thermostable catalysts and their use in electrochemical inventions is found in U.S. Pat. No. 5,665,222 and in PCT Patent Application Publication No. WO 98/35053.

Electrolysis of the Analyte

To electrolyze the analyte, a potential (versus a reference potential) is applied across the working and counter electrodes 58, 60. The minimum magnitude of the applied potential is often dependent on the particular electron transfer agent, analyte (if the analyte is directly electrolyzed at the electrode), or second compound (if a second compound, such as oxygen or hydrogen peroxide, whose level is dependent on the analyte level, is directly electrolyzed at the electrode). The applied potential usually equals or is more oxidizing or reducing, depending on the desired electrochemical reaction, than the redox potential of the electron transfer agent, analyte, or second compound, whichever is directly electrolyzed at the electrode. The potential at the working electrode is typically large enough to drive the electrochemical reaction to or near completion.

The magnitude of the potential may optionally be limited to prevent significant (as determined by the current generated in response to the analyte) electrochemical reaction of interferents, such as urate, ascorbate, and acetaminophen. The limitation of the potential may be obviated if these interferents have been removed in another way, such as by providing an interferent-limiting barrier, as described below, or by including a working electrode 58b (see FIG. 3A) from which a background signal may be obtained.

When a potential is applied between the working electrode 58 and the counter electrode 60, an electrical current will flow. The current is a result of the electrolysis of the analyte or a second compound whose level is affected by the analyte. In one embodiment, the electrochemical reaction occurs via an electron transfer agent and the optional catalyst. Many analytes B are oxidized (or reduced) to products C by an electron transfer agent species A in the presence of an appropriate catalyst (e.g., an enzyme). The electron transfer agent A is then oxidized (or reduced) at the electrode. Electrons are collected by (or removed from) the electrode and the resulting current is measured. This process is illustrated by reaction equations (1) and (2) (similar equations may be written for the reduction of the analyte B by a redox mediator A in the presence of a catalyst):

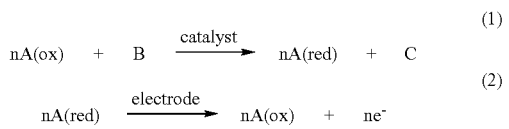

As an example, an electrochemical sensor may be based on the reaction of a glucose molecule with two non-leachable ferricyanide anions in the presence of glucose oxidase to produce two non-leachable ferrocyanide anions, two hydrogen ions, and gluconolactone. The amount of glucose present is assayed by electrooxidizing the non-leachable ferrocyanide anions to non-leachable ferricyanide anions and measuring the current.

In another embodiment, a second compound whose level is affected by the analyte is electrolyzed at the working electrode. In some cases, the analyte D and the second compound, in this case, a reactant compound E, such as oxygen, react in the presence of the catalyst, as shown in reaction equation (3).

The reactant compound E is then directly oxidized (or reduced) at the working electrode, as shown in reaction equation (4)

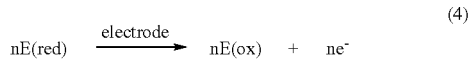

Alternatively, the reactant compound E is indirectly oxidized (or reduced) using an electron transfer agent H (optionally in the presence of a catalyst), that is subsequently reduced or oxidized at the electrode, as shown in reaction equations (5) and (6).

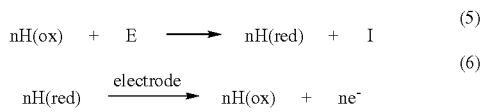

In either case, changes in the concentration of the reactant compound, as indicated by the signal at the working electrode, correspond inversely to changes in the analyte (i.e., as the level of analyte increase then the level of reactant compound and the signal at the electrode decreases.)

In other embodiments, the relevant second compound is a product compound F, as shown in reaction equation (3). The product compound F is formed by the catalyzed reaction of analyte D and then be directly electrolyzed at the electrode or indirectly electrolyzed using an electron transfer agent and, optionally, a catalyst. In these embodiments, the signal arising from the direct or indirect electrolysis of the product compound F at the working electrode corresponds directly to the level of the analyte (unless there are other sources of the product compound). As the level of analyte increases, the level of the product compound and signal at the working electrode increases.

Those skilled in the art will recognize that there are many different reactions that will achieve the same result; namely the electrolysis of an analyte or a compound whose level depends on the level of the analyte. Reaction equations (1) through (6) illustrate non-limiting examples of such reactions.

Temperature Probe

A variety of optional items may be included in the sensor. One optional item is a temperature probe 66 (FIGS. 8 and 11). The temperature probe 66 may be made using a variety of known designs and materials. One exemplary temperature probe 66 is formed using two probe leads 68, 70 connected to each other through a temperature-dependent element 72 that is formed using a material with a temperature-dependent characteristic. An example of a suitable temperature-dependent characteristic is the resistance of the temperature-dependent element 72.

The two probe leads 68, 70 are typically formed using a metal, an alloy, a semimetal, such as graphite, a degenerate or highly doped semiconductor, or a small-band gap semiconductor. Examples of suitable materials include gold, silver, ruthenium oxide, titanium nitride, titanium dioxide, indium doped tin oxide, tin doped indium oxide, or graphite. The temperature-dependent element 72 is typically made using a fine trace (e.g., a conductive trace that has a smaller cross-section than that of the probe leads 68, 70) of the same conductive material as the probe leads, or another material such as a carbon ink, a carbon fiber, or platinum, which has a temperature-dependent characteristic, such as resistance, that provides a temperature-dependent signal when a voltage source is attached to the two probe leads 68, 70 of the temperature probe 66. The temperature-dependent characteristic of the temperature-dependent element 72 may either increase or decrease with temperature. Preferably, the temperature dependence of the characteristic of the temperature-dependent element 72 is approximately linear with temperature over the expected range of biological temperatures (about 25 to 45° C.), although this is not required.

Typically, a signal (e.g., a current) having an amplitude or other property that is a function of the temperature can be obtained by providing a potential across the two probe leads 68, 70 of the temperature probe 66. As the temperature changes, the temperature-dependent characteristic of the temperature-dependent element 72 increases or decreases with a corresponding change in the signal amplitude. The signal from the temperature probe 66 (e.g., the amount of current flowing through the probe) may be combined with the signal obtained from the working electrode 58 by, for example, scaling the temperature probe signal and then adding or subtracting the scaled temperature probe signal from the signal at the working electrode 58. In this manner, the temperature probe 66 can provide a temperature adjustment for the output from the working electrode 58 to offset the temperature dependence of the working electrode 58.

One embodiment of the temperature probe includes probe leads 68, 70 formed as two spaced-apart channels with a temperature-dependent element 72 formed as a cross-channel connecting the two spaced-apart channels, as illustrated in FIG. 8. The two spaced-apart channels contain a conductive material, such as a metal, alloy, semimetal, degenerate semiconductor, or metallic compound. The cross-channel may contain the same material (provided the cross-channel has a smaller cross-section than the two spaced-apart channels) as the probe leads 68, 70. In other embodiments, the material in the cross-channel is different than the material of the probe leads 68, 70.

One exemplary method for forming this particular temperature probe includes forming the two spaced-apart channels and then filling them with the metallic or alloyed conductive material. Next, the cross-channel is formed and then filled with the desired material. The material in the cross-channel overlaps with the conductive material in each of the two spaced-apart channels to form an electrical connection.

For proper operation of the temperature probe 66, the temperature-dependent element 72 of the temperature probe 66 cannot be shorted by conductive material formed between the two probe leads 68, 70. In addition, to prevent conduction between the two probe leads 68, 70 by ionic species within the body or sample fluid, a covering may be provided over the temperature-dependent element 72, and preferably over the portion of the probe leads 68, 70 that is implanted in the patient. The covering may be, for example, a non-conducting film disposed over the temperature-dependent element 72 and probe leads 68, 70 to prevent the ionic conduction. Suitable non-conducting films include, for example, Kapton™ polyimide films (DuPont, Wilmington, Del.).

Another method for eliminating or reducing conduction by ionic species in the body or sample fluid is to use an ac voltage source connected to the probe leads 68, 70. In this way, the positive and negative ionic species are alternately attracted and repelled during each half cycle of the ac voltage. This results in no net attraction of the ions in the body or sample fluid to the temperature probe 66. The maximum amplitude of the ac current through the temperature-dependent element 72 may then be used to correct the measurements from the working electrodes 58.

The temperature probe can be placed on the same substrate as the electrodes. Alternatively, a temperature probe may be placed on a separate substrate. In addition, the temperature probe may be used by itself or in conjunction with other devices.

Biocompatible Layer

Figure 9:
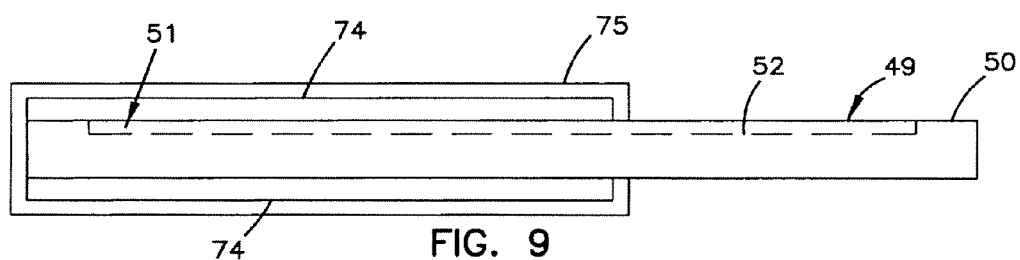
FIG. 9 is a side view of the analyte sensor of FIG. 2.

An optional film layer 75 is formed over at least that portion of the sensor 42 which is subcutaneously inserted into the patient, as shown in FIG. 9. This optional film layer 74 may serve one or more functions. The film layer 74 prevents the penetration of large biomolecules into the electrodes. This is accomplished by using a film layer 74 having a pore size that is smaller than the biomolecules that are to be excluded. Such biomolecules may foul the electrodes and/or the sensing layer 64 thereby reducing the effectiveness of the sensor 42 and altering the expected signal amplitude for a given analyte concentration. The fouling of the working electrodes 58 may also decrease the effective life of the sensor 42. The biocompatible layer 74 may also prevent protein adhesion to the sensor 42, formation of blood clots, and other undesirable interactions between the sensor 42 and body.

For example, the sensor may be completely or partially coated on its exterior with a biocompatible coating. A preferred biocompatible coating is a hydrogel which contains at least 20 wt. % fluid when in equilibrium with the analyte-containing fluid. Examples of suitable hydrogels are described in U.S. Pat. No. 5,593,852, incorporated herein by reference, and include crosslinked polyethylene oxides, such as polyethylene oxide tetraacrylate.

Interferent-Eliminating Layer

An interferent-eliminating layer (not shown) may be included in the sensor 42. The interferent-eliminating layer may be incorporated in the biocompatible layer 75 or in the mass transport limiting layer 74 (described below) or may be a separate layer. Interferents are molecules or other species that are electroreduced or electrooxidized at the electrode, either directly or via an electron transfer agent, to produce a false signal. In one embodiment, a film or membrane prevents the penetration of one or more interferents into the region around the working electrodes 58. Preferably, this type of interferent-eliminating layer is much less permeable to one or more of the interferents than to the analyte.

The interferent-eliminating layer may include ionic components, such as Nafion®, incorporated into a polymeric matrix to reduce the permeability of the interferent-eliminating layer to ionic interferents having the same charge as the ionic components. For example, negatively charged compounds or compounds that form negative ions may be incorporated in the interferent-eliminating layer to reduce the permeation of negative species in the body or sample fluid.

Another example of an interferent-eliminating layer includes a catalyst for catalyzing a reaction which removes interferents. One example of such a catalyst is a peroxidase. Hydrogen peroxide reacts with interferents, such as acetaminophen, urate, and ascorbate. The hydrogen peroxide may be added to the analyte-containing fluid or may be generated in situ, by, for example, the reaction of glucose or lactate in the presence of glucose oxidase or lactate oxidase, respectively. Examples of interferent eliminating layers include a peroxidase enzyme crosslinked (a) using gluteraldehyde as a crosslinking agent or (b) oxidation of oligosaccharide groups in the peroxidase glycoenzyme with $NaIO_4$, followed by coupling of the aldehydes formed to hydrazide groups in a polyacrylamide matrix to form hydrazones are describe in U.S. Pat. Nos. 5,262,305 and 5,356,786, incorporated herein by reference.

Mass Transport Limiting Layer

A mass transport limiting layer 74 may be included with the sensor to act as a diffusion-limiting barrier to reduce the rate of mass transport of the analyte, for example, glucose or lactate, into the region around the working electrodes 58. By limiting the diffusion of the analyte, the steady state concentration of the analyte in the proximity of the working electrode 58 (which is proportional to the concentration of the analyte in the body or sample fluid) can be reduced. This extends the upper range of analyte concentrations that can still be accurately measured and may also expand the range in which the current increases approximately linearly with the level of the analyte.

It is preferred that the permeability of the analyte through the film layer 74 vary little or not at all with temperature, so as to reduce or eliminate the variation of current with temperature. For this reason, it is preferred that in the biologically relevant temperature range from about 25° C. to about 45° C., and most importantly from 30° C. to 40° C., neither the size of the pores in the film nor its hydration or swelling change excessively. Preferably, the mass transport limiting layer is made using a film that absorbs less than 5 wt. % of fluid over 24 hours. This may reduce or obviate any need for a temperature probe. For implantable sensors, it is preferable that the mass transport limiting layer is made using a film that absorbs less than 5 wt. % of fluid over 24 hours at 37° C.

Particularly useful materials for the film layer 74 are membranes that do not swell in the analyte-containing fluid that the sensor tests. Suitable membranes include 3 to 20,000 nm diameter pores. Membranes having 5 to 500 nm diameter pores with well-defined, uniform pore sizes and high aspect ratios are preferred. In one embodiment, the aspect ratio of the pores is preferably two or greater and more preferably five or greater.

Well-defined and uniform pores can be made by track etching a polymeric membrane using accelerated electrons, ions, or particles emitted by radioactive nuclei. Most preferred are anisotropic, polymeric, track etched membranes that expand less in the direction perpendicular to the pores than in the direction of the pores when heated. Suitable polymeric membranes included polycarbonate membranes from Poretics (Livermore, Calif., catalog number 19401, 0.01 μm pore size polycarbonate membrane) and Corning Costar Corp. (Cambridge, Mass., Nucleopore™ brand membranes with 0.015 μm pore size). Other polyolefin and polyester films may be used. It is preferred that the permeability of the mass transport limiting membrane changes no more than 4%, preferably, no more than 3%, and, more preferably, no more than 2%, per ° C. in the range from 30° C. to 40° C. when the membranes resides in the subcutaneous interstitial fluid.

In some embodiments of the invention, the mass transport limiting layer 74 may also limit the flow of oxygen into the sensor 42. This can improve the stability of sensors 42 that are used in situations where variation in the partial pressure of oxygen causes non-linearity in sensor response. In these embodiments, the mass transport limiting layer 74 restricts oxygen transport by at least 40%, preferably at least 60%, and more preferably at least 80%, than the membrane restricts transport of the analyte. For a given type of polymer, films having a greater density (e.g., a density closer to that of the crystalline polymer) are preferred. Polyesters, such as polyethylene terephthalate, are typically less permeable to oxygen and are, therefore, preferred over polycarbonate membranes.

Anticlotting Agent

An implantable sensor may also, optionally, have an anticlotting agent disposed on a portion the substrate which is implanted into a patient. This anticlotting agent may reduce or eliminate the clotting of blood or other body fluid around the sensor, particularly after insertion of the sensor. Blood clots may foul the sensor or irreproducibly reduce the amount of analyte which diffuses into the sensor. Examples of useful anticlotting agents include heparin and tissue plasminogen activator (TPA), as well as other known anticlotting agents.

The anticlotting agent may be applied to at least a portion of that part of the sensor 42 that is to be implanted. The anticlotting agent may be applied, for example, by bath, spraying, brushing, or dipping. The anticlotting agent is allowed to dry on the sensor 42. The anticlotting agent may be immobilized on the surface of the sensor or it may be allowed to diffuse away from the sensor surface. Typically, the quantities of anticlotting agent disposed on the sensor are far below the amounts typically used for treatment of medical conditions involving blood clots and, therefore, have only a limited, localized effect.

Sensor Lifetime

The sensor 42 may be designed to be a replaceable component in an in vivo or in vitro analyte monitor, and particularly in an implantable analyte monitor. Typically, the sensor 42 is capable of operation over a period of days. Preferably, the period of operation is at least one day, more preferably at least three days, and most preferably at least one week. The sensor 42 can then be removed and replaced with a new sensor. The lifetime of the sensor 42 may be reduced by the fouling of the electrodes or by the leaching of the electron transfer agent or catalyst. These limitations on the longevity of the sensor 42 can be overcome by the use of a biocompatible layer 75 or non-leachable electron transfer agent and catalyst, respectively, as described above.

Another primary limitation on the lifetime of the sensor 42 is the temperature stability of the catalyst. Many catalysts are enzymes, which are very sensitive to the ambient temperature and may degrade at temperatures of the patient's body (e.g., approximately 37° C. for the human body). Thus, robust enzymes should be used where available. The sensor 42 should be replaced when a sufficient amount of the enzyme has been deactivated to introduce an unacceptable amount of error in the measurements.

Manufacturing Process—Substrate and Channel Formation

Figure 12:
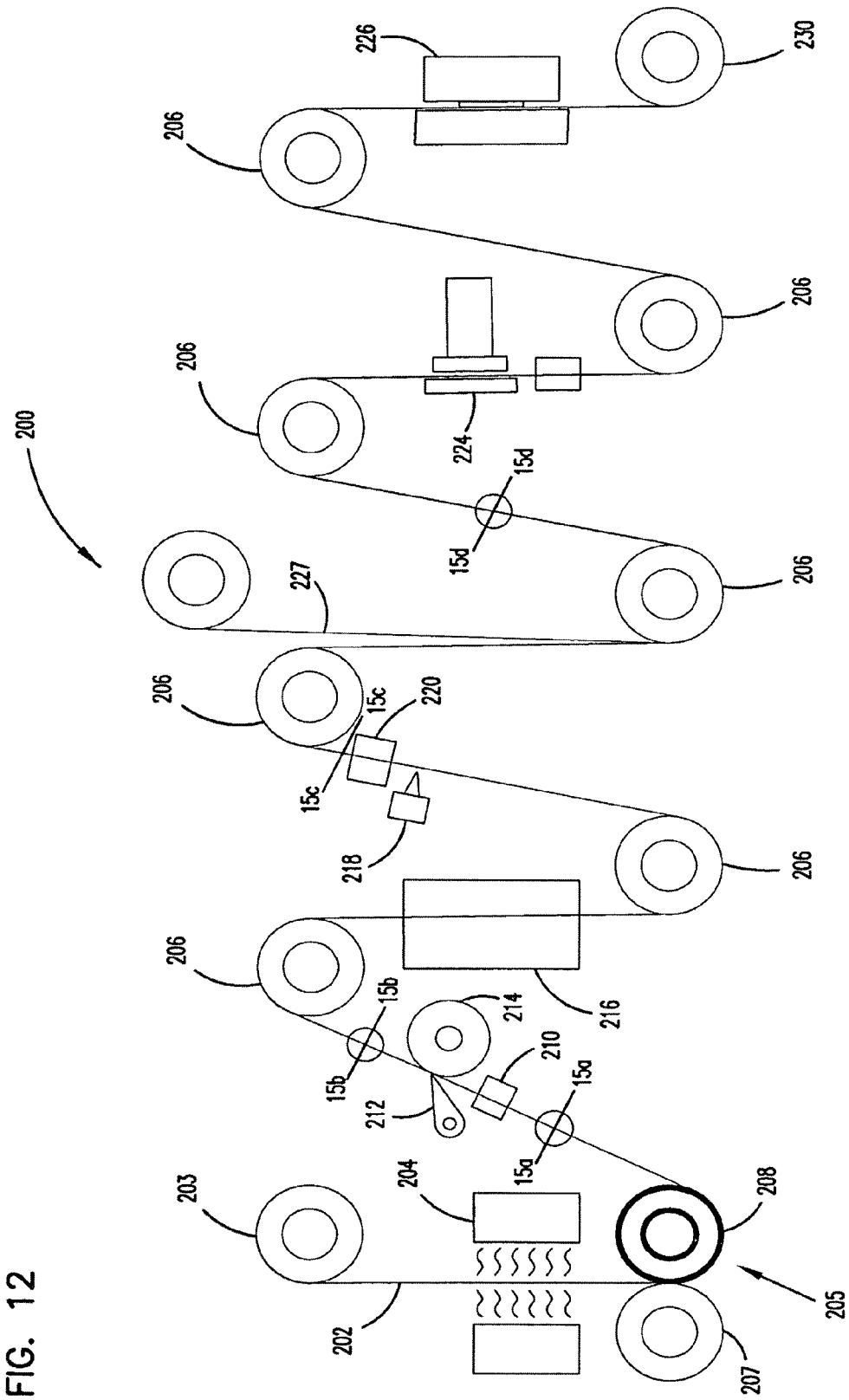
FIG. 12 is a schematic illustration of an exemplary method or system for manufacturing the sensor of FIG. 2.

FIG. 12 is a schematic illustration of an exemplary system 200, in accordance with the principles of the present invention, for manufacturing the sensor 42. The system 200 utilizes a continuous film or substrate web 202 that is guided along a serpentine pathway by a series of rollers 206. Along the pathway, the web 202 is processed at the various processing stations or zones. For example, at one station channels can be formed in the web 202. At subsequent stations, conductive material can be placed in the channels, sensor chemistry can be deposited over portions of the conductive material corresponding with working electrodes, and a protective film or micro-porous membrane can be affixed to the web 202. At a final step, the sensor 42 can be cut, stamped or otherwise removed from the continuous web 202. A more detailed description of the various steps is provided in the following paragraphs.

The continuous substrate web 202 ultimately forms the substrate 50 of the sensor 42. Consequently, for certain applications, the web 202 is made of nonconducting plastic or polymeric materials such as those previously identified in the specification with respect to the substrate 50. In one particular embodiment, the web 202 comprises a continuous plastic or polymeric film having a thickness in the range of 50 to 500 μm (2-20 mil), and preferably in the range of 100 to 300 μm (4-12 mil).

To initiate the manufacturing process, the web 202 is pulled from a source reel 203 and passed through a heater 204. As shown in FIG. 12, the heater 204 includes two heated platens arranged and configured to allow the web 202 to pass between parallel heated surfaces at a predetermined feed rate and distance. For many applications, the web 202 is heated to a sufficient temperature, for example, to a glass transition temperature of the substrate web 202 to soften the web 202 in preparation for subsequent embossing or stamping steps.

With respect to the heating step, it will be appreciated that certain web materials may have sufficient deformability to allow channels to be pressed therein without requiring a heating step. Similarly, if no channels are desired to be formed in the web 202, or channels are to be formed through non-mechanical techniques such as laser or chemical etching, the initial heating step can also be eliminated from the process. Furthermore, if it is desired to soften the web 202 via heat, it will be appreciated that any number of known heating sources/configurations, such as radiant or convection heaters, can be utilized. Alternatively, the forming tool may be heated and not the web.

After the web 202 has been heated to a desired temperature by the heater 204, the web 202 is preferably conveyed to a channel formation station/zone 205 where the channels 54 are preferably mechanically pressed into the web 202 by a continuous embossing process. For example, as shown in FIG. 12, the channels 54 of the sensor 42 are formed in the web 202 by pressing the web 202 between a flat roller 207 and an embossing roller 208 having a desired embossing pattern formed on its outer surface. As the web 202 passes between the rollers 207 and 208, a desired channel pattern is stamped, embossed, formed or otherwise pressed into one side of the web 202. During the embossing step, an outline or planform of the sensor 42, as shown in FIG. 2, can optionally be pressed into the web 202 to generate perforations that extend partially through the web 202. In one particular embodiment, the web 202 is perforated to a depth of about 70% of the thickness of the web 202. Alternatively, about 70% of the perimeter of the planform is completely perforated. Perforating the web 202 facilitates subsequently removing the sensor 42 and provides the advantage of lessening registration constraints at later stages of the manufacturing process.

Figure 15A:
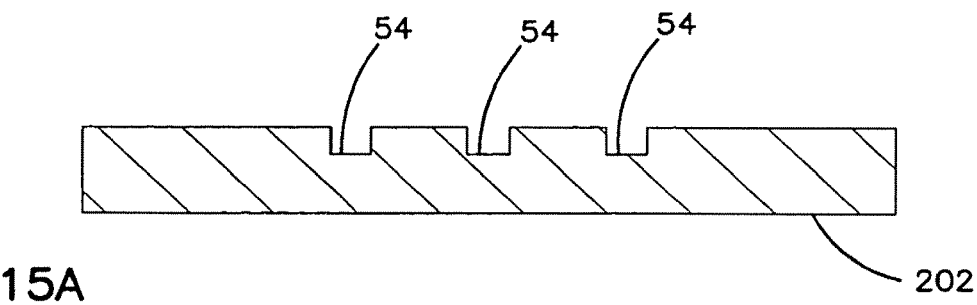
FIG. 15A is cross sectional view taken along section line 15$a$-15$a$ of FIG. 12.

FIG. 15A is a cross-sectional view taken through the web 202 immediately after the sensor channels 54 have been formed within the web 202. As shown in FIG. 15A, the channels 54 are generally uniformly spaced across the width of the web 202 and have generally rectangular cross-sectional profiles. The width of the channels may be in the range of about 25 to about 250 µm. In one particular embodiment of the present invention, the channels have individual widths of 250 µm (about 8 mils), 150 µm, 100 µm, 75 µm, 50 µm, 25 µm or less. The depth of the channels is typically related to the thickness of the web 202. In one embodiment, the channels have depths in the range of about 12.5 to 75 µm (0.5 to 3 mils), and preferably about 25 to 50 µm (1 to 2 mils). The distance between the conductive traces may be in the range of about 25 to 150 µm, and may be, for example, 150 µm, 100 µm, 75 µm, 50 µm, or less. The density of the conductive traces 52 on the substrate 50 may be in the range of about 150 to 700 ™ and may be as small as 667 µm/trace or less, 333 µm/trace or less, or even 167 µm/trace or less.

Figure 13:
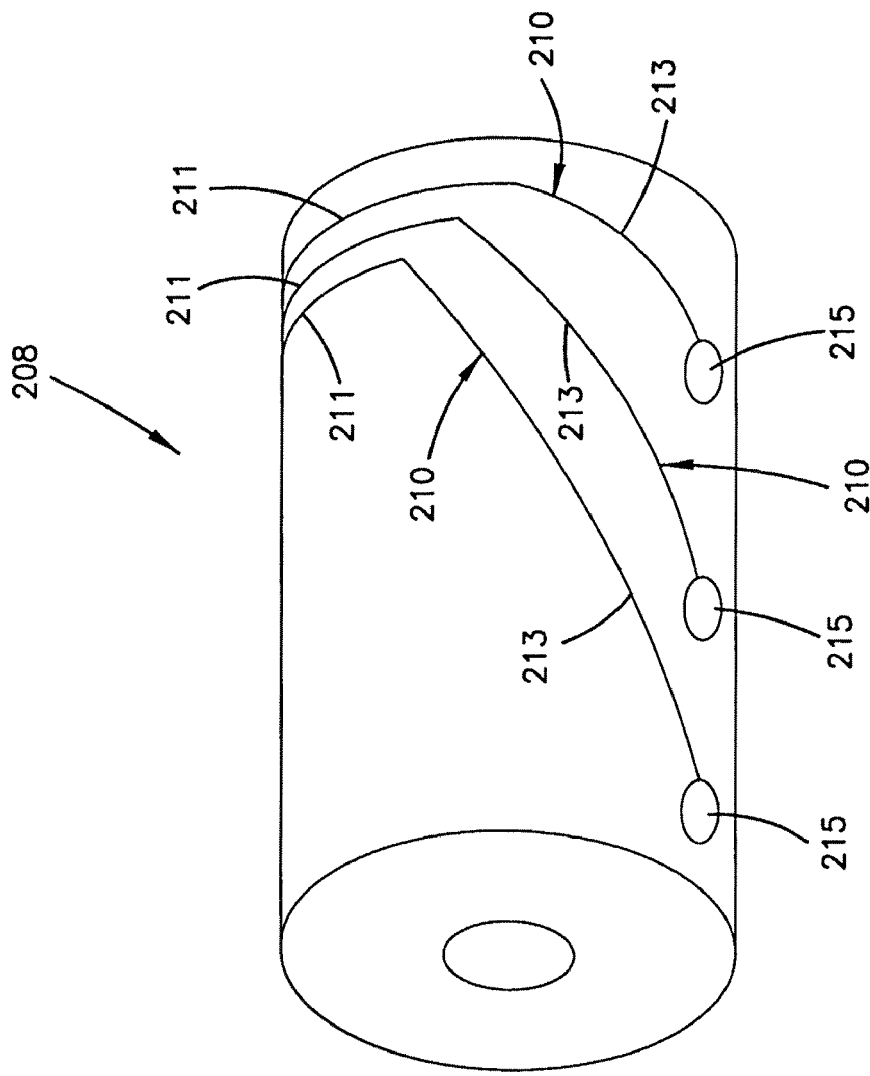
FIG. 13 is a perspective view of an exemplary embossing roller suitable for use in the system of FIG. 12.

It will be appreciated that embossing rollers suitable for use with the present invention can be designed to form a wide range of different channel patterns. For example, FIG. 13 provides a perspective view of one embossing roller 208 that is adapted for forming the channel configuration of the sensor 42. As shown in FIG. 13, the embossing stamp or roller 208 includes a pattern of raised members or portions 210 that project radially outward from the outer surface of the roller 208. The raised portions 210 extend about the circumference of the roller 208 and are arranged in a configuration that corresponds to the desired channel configuration shown in FIG. 2. Specifically, the raised portions 210 include generally parallel, relatively closely spaced raised lines 211 corresponding to the channel pattern desired to be formed along the narrow portion 67a of the sensor 42. The raised portions 210 also include angled or diverging/converging raised lines 213 corresponding to the channel pattern desired to be formed along the wider portion 65a of the sensor 42. In certain embodiments, the raised lines 211 and 213 have widths less than about 150 microns, preferably less than about 100 microns, and most preferably less than about 50 microns.

The raised portions 210 further include tabs or punch members 215 adapted for forming contact pad depressions in which conductive material can be disposed to form the contact pads 49 of the sensor 42. When the web 202 is pressed against the outer surface of the roller 208, the raised portions 210 project or extend into the web 202 causing the web 202 to deform or indent such that the channels 54 and contact pad depressions are formed within the web 202. In other words, the raised portions 210 of the roller 208 form a pattern of depressions in the web 202 that includes such features as the channels 54 and the contact pad depressions.

As shown in FIG. 13, a single embossing pattern is disposed on the outer surface of the roller 208. However, it will be appreciated that by enlarging the diameter of the roller 208, multiple identical patterns can be arranged about the circumference of the roller. Furthermore, multiple different patterns can be arranged about the circumference of the roller to allow different sensor configurations to be manufactured with a single embossing roller.

Figure 14:
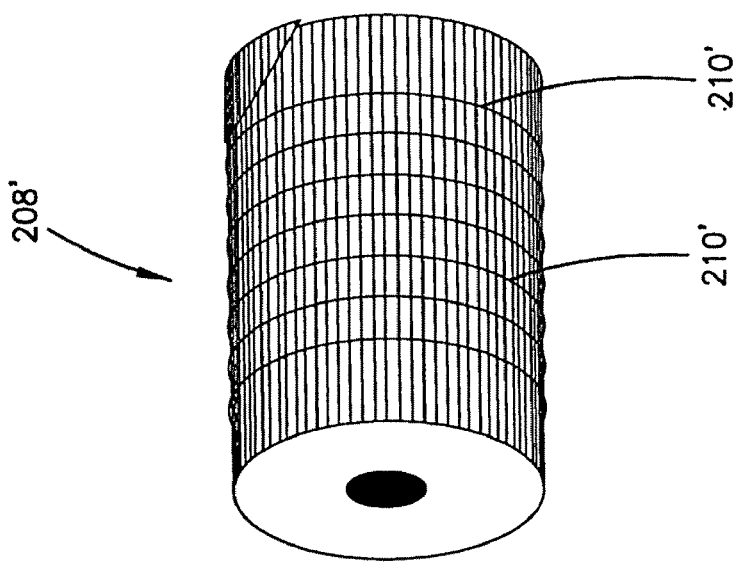
FIG. 14 is a perspective of an alternative embossing roller.

Referring now to FIG. 14, an alternative roller 208' is illustrated. The alternative roller 208' includes a plurality of raised annular rings 210' that extend about the circumference of the roller 208'. Each ring 210' can extend continuously about the entire circumference of the roller 208', or can be separated into discrete segments by gaps located at predetermined intervals about the roller 208'. The roller 208' is adapted to form a plurality of substantially parallel, straight channels in the web 202. One use of such a roller 208' relates to the manufacture of sensors having substantially constant widths.

It will be appreciated that embossing tools suitable for use with the present invention, such as rollers, presses or stamps, can be manufactured using a variety of techniques. For example, such tools can be molded, formed or cast using conventional techniques. Exemplary materials for making such embossing tools include steel and other metals, minerals such as sapphire and silicon, epoxides, ceramics, and appropriate polymers.

In one particular embodiment of the present invention, silicon is used to make an embossing tool such as an embossing roller or stamp. Preferably, a desired pattern of raised portions is formed on the embossing surface of the tool using photolithographic and etching techniques to remove selected portions of the tool. It has been determined that such a process can yield an embossing tool having a desirable surface finish, precisely shaped features at small sizes, no burrs, and sharp features (e.g., small radii between intersecting features).

Silicon is preferred for a flat (non-cylindrical) tool, and may be etched using techniques common to the integrated circuit industry to create profiles in the wafer surface. Such profiles may be either positive in relief above the surface or negative below the wafer surface. Positive profiles may be used directly as tools to create indentations in a softer substrate. Negative profiles may be used as a master to create a series of second generation positives that are used as the final tool. The second generation positives may be made from any castable material with the appropriate mechanical properties.

Manufacturing Process—Formation of Conductive Traces

Referring back to FIG. 12, after the channels 54 of the sensor 42 have been formed in the web 202, the web 202 is conveyed to a channel filling station/zone 210 where conductive material is placed, flowed, applied, filled, flooded or otherwise disposed within the channels 54. For certain applications, the conductive material can be applied as a precursor conductive material having a liquid form. An exemplary precursor conductive material includes conductive material dissolved or suspended in a solvent or dispersant. A preferred precursor conductive material is a carbon based ink that can be flooded in liquid form into the channels 54. Other conductive inks or pastes that include carbon or metal, such as, for example, gold, copper, or silver, may be used. Other techniques for applying the conductive material or precursor conductive material include spraying, coating, flooding, applying with a saturated roller, pumping, as well as electrostatic, ionographic, magnetographic, and other impact and non-impact printing methods.

After the channels 54 have been substantially filled with conductive material or precursor conductive material, the web 202 is preferably passed through an arrangement/device for scraping or wiping excess conductive material/precursor conductive material from the surface of the web 202. For example, as shown in FIG. 12, a coating blade 212 and roller 214 are used to remove excess material from the web 202. After the web 202 has passed by the coating blade 212 and roller 214, the conductive material/precursor conductive material substantially fills the channels 54 such that the web and conductive material/precursor conductive material together form a substantially flat or planar surface.

Figure 15B:
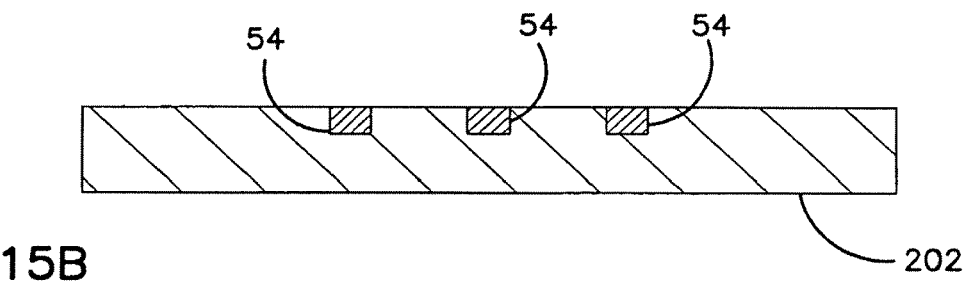
FIG. 15B is a cross sectional view taken along section line 15$b$-15$b$ of FIG. 12.

FIG. 15B shows a cross section through the web 202 after the excess conductive material/precursor conductive material has been wiped from the web 202. While it is preferred for the channels 54 to be substantially filled with the conductive material/precursor conductive material, it will be appreciated that in certain embodiments it may be desirable to only partially fill the channels 54, or to slightly overfill the channels 54 with conductive material/precursor conductive material.

As shown in FIG. 12, a single series of channel forming, filling and wiping steps are used to fill the channels 54. It will be appreciated that in alternative embodiments, multiple channel formation, filling and wiping steps can be utilized to fill channels formed in the substrate 50. For example, to manufacture the sensor 42 of FIG. 2, it may be desirable to utilize two separate channel formation steps, and two separate filling and wiping steps. In such a process, the reference electrode channel could initially be formed in the substrate, and then filled with a suitable conductive material such as silver/silver chloride. Subsequently, the working electrode channels of the sensor 42 could be formed in the substrate and filled with a conductive material such as carbon. Separating the various channel formation, filling and wiping steps can assist in inhibiting cross contamination of conductive materials between the various electrodes. Of course, the particular sequence of processing steps identified herein are strictly exemplary and should not be construed as a limitation upon the scope of the present invention.

Manufacturing Process—Other Methods for Forming Conductive Traces

In addition to the above identified mechanical techniques for forming the channels 54 in the web 202, other techniques can also be utilized. For example, the channels can be formed by removing or carbonizing a portion of the substrate 50 or web 202 using a laser, or photolithographic patterning and etching of the substrate 50 or web 202. Furthermore, for certain applications, channels may not be formed in the substrate 50 or web 202 at all. For example, as discussed above, the conductive traces 52 can be formed on the substrate 50 by a variety of techniques, including photolithography, screen printing, other printing techniques, stamping traces into the substrate or web 202, or using a laser to micro-machine traces into the substrate 50 or web 202. Each of these techniques has corresponding limits on the reproducibility, precision, and cost of producing the conductive traces.

Another method for forming the conductive traces uses techniques common to pad printing or hot stamping methods, whereby a film of conductive material is formed, for example, as a continuous sheet or as a coating layer deposited on a carrier film. The film of conductive material is brought between a print head and the substrate 500. A pattern of conductive traces 52 is formed on the substrate 50 using the print head. The conductive material is transferred by pressure and/or heat from the conductive film to the substrate 50. This technique may produce channels (e.g., depressions caused by impact of the print head on the substrate 50). Alternatively, the conductive material is deposited directly without forming substantial depressions in the surface of the substrate 50.

In other embodiments, the conductive traces 52 are formed by non-impact printing techniques. These methods do not require the formation of channels in the substrate. Instead, conductive traces may be formed directly on a planer substrate. Such techniques include electrophotography and magnetography. In these processes, an image of the conductive traces 52 is electrically or magnetically formed on a drum. A laser or LED may be used to electrically form the image or a magnetic recording head may be used to magnetically form the image. A toner material (e.g., a conductive material, such as a conductive ink) is then attracted to portions of the drum according to the image. The toner material is then applied to the substrate by contact between the drum and the substrate. For example, the substrate may be rolled over the drum. The toner material may then be dried and/or a binder in the toner material may be cured to adhere the toner material to the substrate.

Another non-impact printing technique includes ejecting droplets of conductive material onto the substrate in a desired pattern. Examples of this technique include ink jet printing and piezo jet printing. An image is sent to the printer which then ejects the conductive material (e.g., a conductive ink) according to the pattern. The printer may provide a continuous stream of conductive material or the printer may eject the conductive material in discrete amounts at the desired points.

Yet another embodiment of forming the conductive traces includes an ionographic process. In this process, a curable, liquid precursor, such as a photopolymerizable acrylic resin (e.g., Solimer 7501 from Cubital, Bad Kreuznach, Germany), is deposited over a surface of a substrate 50. A photomask having a positive or negative image of the conductive traces 52 is then used to cure the liquid precursor. Light (e.g., visible or ultraviolet light) is directed through the photomask to cure the liquid precursor and form a solid layer over the substrate according to the image on the photomask. Uncured liquid precursor is removed leaving behind channels 54 in the solid layer. These channels 54 can then be filled with conductive material 56 to form conductive traces 52.

Manufacturing Process—Drying and Curing

Once the web 202 has been wiped by the coating blade 212 and roller mechanism 214, the web 202 is moved through a drying chamber 216. The drying chamber 216 preferably provides sufficient heat to drive off or evaporate solvents or dispersants that may be contained in precursor conductive material within the channels 54. After heating, conductive material is preferably left as a residue in the channels 54. In certain cases, the drying chamber 216 exposes the web 202 to sufficient temperatures to cure optional binders that may be present with the conductive material. It will be appreciated that ultraviolet light could also be used to cure optional binders interspersed with the conductive material.

Manufacturing Process—Sensor Chemistry Deposition

Figure 15C:
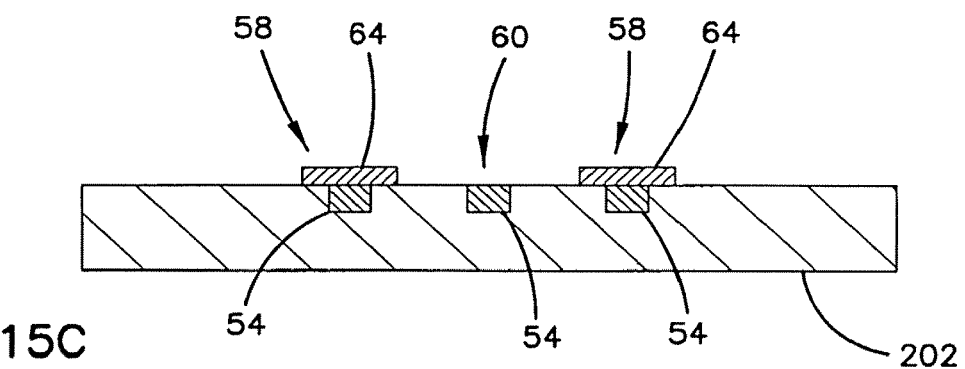
FIG. 15C is a cross sectional view taken along section line 15$c$-15$c$ of FIG. 12.
Figure 15D:
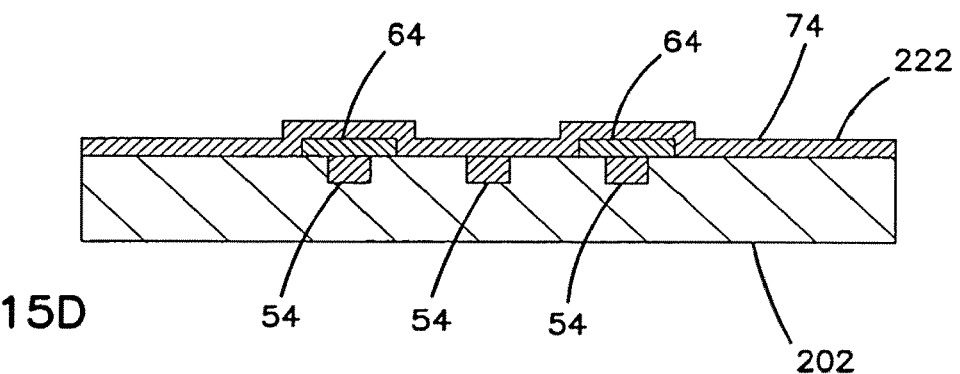
FIG. 15D is a cross sectional view taken along section line 15$d$-15$d$ of FIG. 12.

After the web 202 has been heated in the heating chamber 216, the web 202 is directed to a sensor chemistry deposition station/zone 218 at which sensor chemistry is deposited, placed, or otherwise disposed over portions of the conductive material within the channels 54 so as to form the sensing layers 64 over the working electrodes 58. FIG. 15C is a cross-sectional view cut through the web 202 after the sensor chemistry has been deposited on the web 202. As shown in FIG. 15C, sensor chemistry is only deposited over the conductive material corresponding to the working electrodes 58, which in one embodiment, as illustrate in FIG. 4A, are formed at the two outer channels 54. Consequently, a relatively precise application technique is preferably used to inhibit sensor chemistry from being applied to both the working electrodes 58 and electrodes that should not be coated. It is acceptable, in some situations, for the sensing layer to also coat the counter electrode 60.

It will be appreciated that a variety of techniques can be used to apply or deposit the sensor chemistry on the web 202.

In one particular embodiment of the present invention, piezo jet technology or the like is used to deposit the chemistry upon the web 202 to form the sensing layers 64. A solenoid valve can be rapidly shuttered and when supplied with liquid under a precisely controlled over-pressure condition, a droplet of controlled size will be ejected from the valve. Resolutions to 500 picoliters can be achieved. Conventional ink jet printers can also be used.

To enhance adhesion of the sensor chemistry to the web 202, the surface of the web 202 can optionally be roughened by techniques such as abrasion or plasma treatment prior to applying the sensor chemistry. For example, by pre-treating the surface of the web 202, for example, by a corona discharge, free radicals are generated on the web surface to enhance adhesion of the sensor chemistry to the web 202 and working electrodes 58.

Once the sensor chemistry has been applied to the web 202, the web 202 is preferably conveyed through another heating chamber 220. The heating chamber 220 preferably provides sufficient temperature/heating to release solvents from the deposited sensor chemistry. The heating chamber 220 can also heat the web 202 to sufficient temperatures to cause potential polymerization reactions such as cross link reactions between polymers and the redox mediator and/or redox enzyme.

Manufacturing Process—Membrane Layer

Upon exiting the heating station 220, the substrate web 202 is brought into alignment with a membrane web 222 adapted for forming a membrane layer, that may include one or more individual membranes, such as a mass transport limiting layer 74 or a biocompatible layer 75, over at least some portions of the electrodes. The membrane layer may be applied to only one or two or more surfaces of the substrate. For certain embodiments, solvents such as methyl ethyl ketone and acetone can be applied, for example, sprayed, on the web 202 to soften the web 202 and solvent bond it to the membrane web 222. By heating the solvent after the web 202 has been brought in contact with the membrane web 222, the two webs 202 and 222 can be bonded together such that the web 222 covers and protects portions of the sensor adapted to be implanted. Alternatively, the two webs 202 and 222 can be bonded or fused together at a welding station 224 such as a sonic or laser welding station. The resultant combination of the substrate web 202 and the membrane web 222 results in a laminated structure in which the protective membrane 74 is selectively fused to the polymer substrate 50. In some embodiments, individual membrane webs 222 are bonded to two or more surfaces of the web 202.

The membrane layer may include one or membranes that individually or in combination serve a number of functions. These include protection of the electrode surface, prevention of leaching of components in the sensing layer, mass transport limitation of the analyte, exclusion of interfering substances, reduction or enhancement of oxygen mass transport, and/or biocompatibility. In one embodiment, a membrane is selected which has mass transport limiting pores that do not change appreciably in size over a physiologically relevant temperature range (e.g., 30° C. to 40° C.). This may reduce the temperature dependence of the sensor output.

Manufacturing Process—Cutting

As a final step in the sequence 200, the laminated webs 202 and 222 enter a cutting station/zone 226 in which the sensor 42 planform, as shown in FIG. 2, is cut from the continuous webs 202 and 222. For example, the cutting station 226 can include a die stamper, embosser, embossing roller, laser cutter or any other mechanism for cutting, pressing or otherwise removing the sensors 42 from the webs 202 and 204. This cutting step may result in discrete sensor components or the sensors may be partially cut out and retained on the webs for secondary operations such as surface mounting of electronic components or packaging. A take-up reel 230 accumulates the web material remaining after the sensors 42 have been cut from the web.

Multiple Traces/Multiple Surfaces

Figure 16:
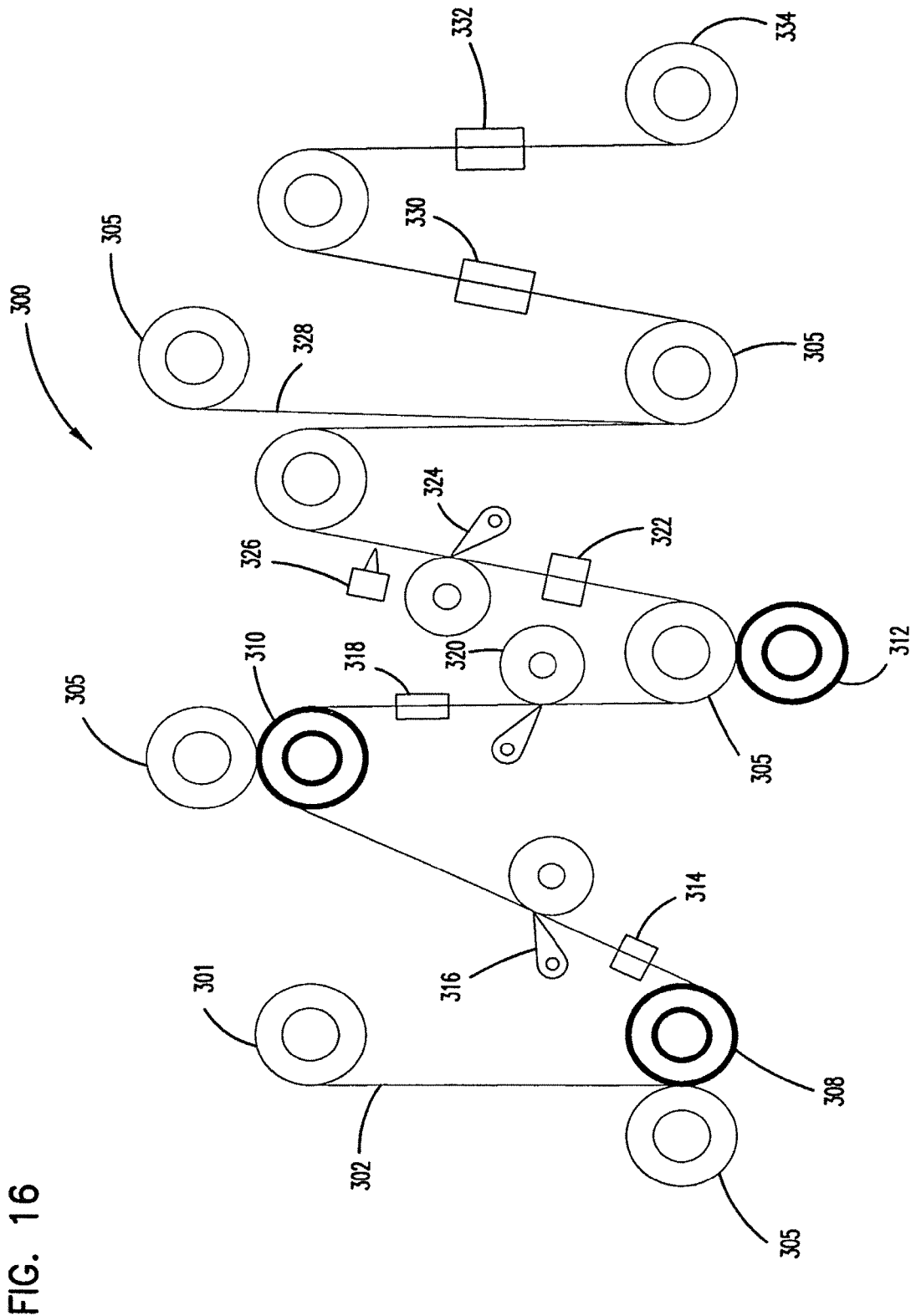
FIG. 16 illustrates a system in accordance with the principles of the present invention for making the sensor of FIGS. 10 and 11.

FIG. 16 is a schematic illustration of an exemplary system 300, in accordance with the principles of the present invention, for manufacturing the sensor 42 of FIGS. 6-8 and 10-11. The system 300 utilizes a continuous film or web 302 that is guided along a serpentine pathway by a series of rollers 305. To provide channels on opposite sides of the web 302, the system utilizes a series of embossing steps. For example, the system 300 includes a first embossing roller 308 configured for forming the channels for the working and counter electrode 58, 60, respectively, in a first side of the web 302, a second embossing roller 310 configured for forming the channel for the temperature probe/sensor 66 and the reference electrode 62 in a second opposite side of the web 302, and a third embossing roller 312 configured for forming the channel for the temperature-dependent element 72 extending between the channels for the two temperature probe leads 68, 70. In a preferred embodiment, opposing embossing rollers are used to emboss both sides simultaneously in a single step.

In basic operation of the system, the web 302 is first pulled from a spool or reel 301 and preferably heated. Next, the channels for the working electrode and counter electrodes 58, 60 are formed in the first side of the web 302 by the first embossing roller 308. It will be appreciated that the first embossing roller 308 preferably includes a pattern of raised portions having a configuration that corresponds to the channel configuration depicted in FIG. 7. Thereafter, the channels of the working and counter electrodes 58, 60 are filled with conductive material/precursor conductive material, such as a flowable conductive carbon ink, at a first channel filling station 314. Subsequently, excess conductive material/precursor conductive material is wiped from the web 302 by a first web wiping arrangement 316.

Once the channels for the working and counter electrodes 58, 60 have been filled with conductive material/precursor conductive material and wiped, the opposite second side of the web 302 is embossed by the second embossing roller 310 such that the channels for the temperature probe leads 68, 70 and the reference electrode 62 are formed in the opposite side of the web 302. It will be appreciated that the second embossing roller 310 preferably includes a pattern of raised portions having a configuration that corresponds to the channel configuration depicted in FIG. 8 (except for channel for the temperature-dependent element 72). It will also be appreciated that the embossing roller 310 can be equipped with projections or punch members for forming vias through the web 302 at desired pad 49 locations of the sensor 42.

After the channels for the temperature probe leads 68, 70 and reference electrode 72 have been formed in the web 202, such channels are filled with suitable conductive material/precursor conductive material at a second channel filling station 318 and excess conductive material/precursor conductive material is wiped from the web 302 at wiping mechanism 320. While one filling station 318 is shown for filling both channels for the temperature probe leads 68, 70 and the reference electrode 62, it will be appreciated that the filling station 318 may include multiple separate filling steps for individually or separately filling each channel.

Once the channels for the temperature probe leads 68, 70 and reference electrode 62 have been filled with conductive material/precursor conductive material and wiped, the channel for the temperature-dependent element 72 of the temperature probe 66 is formed between the channels for the temperature probe leads 68, 70 by the third embossing roller 312. Subsequently, the channel for the temperature-dependent element 72 is filled with appropriate material at channel filling station 322, and excess material is wiped from the web 302 by wiping mechanism 324.

Once both sides of the web 302 have been filled with the appropriate conductive and/or resistive material, sensor chemistry is applied to the working electrodes 58 at a sensor chemical application station 326. The sensor chemistry can be applied at the sensor chemical application station 326 by a variety of techniques. Exemplary techniques include piezo jet printing, ink jet printing, spraying, flowing the sensor chemistry onto the electrodes, coating chemistry on the electrodes, or any other technique suitable for applying chemistry to a relatively precise location. As shown in FIG. 7, to reduce the required printing precision, the working electrodes 58 optionally have ends that are staggered with respect to the end of the counter electrode 60. Such a configuration assists in inhibiting the sensor chemistry from unintentionally being applied to the counter electrode 60.

As a next step in the process, a protective membrane web 328 is then bought into contact with the substrate web 302 such that at least portions of the working and counter electrodes 58 and 60 are covered by the membrane 328. At membrane bonding station 330, the protective membrane 328 and the substrate web 302 are bonded or fused together by techniques such as solvent bonding, adhesive bonding, laser bonding, laser welding, and/or sonic welding. In the case of solvent bonding, the solvent is applied before the protective membrane is brought into contact with the substrate web. A second membrane may optionally be laminated onto the opposing side of the substrate web to protect the reference electrode and temperature probe. The resulting laminate structure that exits the membrane bonding station 330 is conveyed to a cutting station 332 in which individual discrete planforms of the sensor 42" are cut, pressed, stamped or otherwise separated from the continuous web 302. For certain applications, it may be desirable to only partially cut the individual sensor planforms from the web 302 such that the sensors are retained on the web for secondary operations. Remaining web material is taken up by take-up reel 334.

It will be appreciated that the particular operating sequence illustrated in FIG. 16 is strictly exemplary and that variations can be made in the number of steps and the sequence of steps without departing from the principles of the present invention. Additionally, although not shown in FIG. 16, various heating or energy dispersive stations can be placed at locations along the web pathway to heat the web 302 for such purposes as plasticizing the substrate web 302 prior to embossing, curing binders contained within conductive material deposited within the channels of the sensors, and evaporating solvents or dispersants. Furthermore, although FIGS. 12 and 16 each relate to continuous web processes, it will be appreciated that the present invention is not limited to continuous web processes. For example, the various process steps disclosed herein can be performed with respect to discrete or individual sensors completely separate from a web. Sheet fed processing may also be employed as an alternative to a continuous web. Moreover, while in certain embodiments of the present invention the web can be moved continuously through various processing steps at a substantially constant speed, in other embodiments the web can be intermittently stopped and started, or the speed of the web can be varied.

The process of the invention for the manufacture of sensors is rapid and efficient. The process of the invention can produce approximately 5000 conductive traces per hour. Within batch variation of the sensors will be less than between batch variation, thus it is desirable to produce the sensors in large batches. For example, batches of 100 or more or of 1000 or more sensors may be produced.

The sensor may be provided with a code, for example a batch code, during processing. The code may be applied to the sensor, for example by printing the code on the substrate. The sensor code may include information such as the batch number, the type and quantity of chemistry applied to the sensor, and/or calibration data.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. The claims are intended to cover such modifications and devices.

We claim:

1. An analyte sensor, comprising:
   a substrate having a proximal end portion having a width defined by a first side and a second side, and a distal end portion having a width defined by a third side and a fourth side, the width of the distal end portion being less than the width of the proximal end portion, the distal end portion being adjacent to the proximal end portion and extending therefrom;
   one or more electrodes formed on the substrate, the one or more electrodes including an analyte-response enzyme and a mediator, wherein at least one of the analyte-response enzyme and the mediator is chemically bound to a polymer disposed on the one or more electrodes; and
   at least two traces separated by a distance of about 25 microns to about 250 microns, wherein at least one trace has a width of about 25 microns to 250 microns;
      wherein the flexibility of the sensor is varied based on a composition or thickness of the sensor; and
      wherein the first side and the third side together form a continuous straight edge and the second side and the fourth side do not form a continuous straight edge.

2. The sensor of claim 1, wherein the at least two traces are separated by a distance of about 100 microns or less.

3. The sensor of claim 2, wherein the at least one trace has a width of about 75 microns or less.

4. The sensor of claim 3, wherein the at least one trace has a width of about 50 microns or less.

5. The sensor of claim 1, wherein the sensor is coupled to a skin piercer.

6. The sensor of claim 5, wherein the sensor separates from the skin piercer after positioning.

7. The sensor of claim 1, comprising a varying width.

8. The sensor of claim 1, wherein the one or more electrodes includes two or more electrodes.

9. The sensor of claim 8, wherein two of the two or more electrodes are working electrodes.

10. The sensor of claim 1, wherein the at least two traces are on the same side of the substrate.

11. The sensor of claim 1, wherein the flexibility of the sensor is varied along a continuum of the sensor.

12. The sensor of claim 1, wherein the sensor includes a code applied to the sensor.

13. The sensor of claim 12, wherein the code is printed on a substrate of the sensor.

14. The sensor of claim 12, wherein the code includes one or more of a batch number, a quantity of chemistry applied to the sensor, or calibration data.

15. The sensor of claim 12, wherein the code is applied to the sensor during manufacturing.

* * * * *